(12) United States Patent
Erbilgin et al.

(10) Patent No.: US 11,948,662 B2
(45) Date of Patent: Apr. 2, 2024

(54) METABOLITE, ANNOTATION, AND GENE INTEGRATION SYSTEM AND METHOD

(71) Applicant: The Regents of the University of California, Oakland, CA (US)

(72) Inventors: Onur Erbilgin, Oakland, CA (US); Benjamin P. Bowen, Walnut Creek, CA (US); Trent R. Northen, Walnut Creek, CA (US); Markus de Raad, Berkeley, CA (US); Oliver Ruebel, Richmond, CA (US)

(73) Assignee: The Regents of the University of California, Oakland, CA (US)

(*) Notice: Subject to any disclaimer, the term of this patent is extended or adjusted under 35 U.S.C. 154(b) by 411 days.

(21) Appl. No.: 15/932,459

(22) Filed: Feb. 16, 2018

(65) Prior Publication Data
US 2018/0239863 A1 Aug. 23, 2018

Related U.S. Application Data

(60) Provisional application No. 62/578,956, filed on Oct. 30, 2017, provisional application No. 62/460,680, filed on Feb. 17, 2017.

(51) Int. Cl.
| | | |
|---|---|---|
| *G16H 70/60* | (2018.01) | |
| *G01N 33/00* | (2006.01) | |
| *G06F 16/903* | (2019.01) | |
| *G16B 5/00* | (2019.01) | |
| *G16B 20/00* | (2019.01) | |
| *G16C 20/20* | (2019.01) | |

(52) U.S. Cl.
CPC ............ *G16B 20/00* (2019.02); *G01N 33/00* (2013.01); *G06F 16/903* (2019.01); *G16B 5/00* (2019.02); *G16H 70/60* (2018.01); *G16C 20/20* (2019.02); *Y02A 90/10* (2018.01)

(58) Field of Classification Search
CPC .......... G16B 20/00; G16B 5/00; G16H 70/60; G06F 16/903; G01N 33/00
USPC ........................................................ 705/2, 3
See application file for complete search history.

(56) References Cited

U.S. PATENT DOCUMENTS

| | | | |
|---|---|---|---|
| 6,444,221 B1* | 9/2002 | Shapiro ................ | A61K 31/195 424/451 |
| 6,849,442 B1* | 2/2005 | Archer ................. | C12Q 1/6897 536/23.1 |

(Continued)

OTHER PUBLICATIONS

Allen, F., Greiner, R. & Wishart, D. Competitive fragmentation modeling of ESI-MS/MS spectra for putative metabolite identification. *Metabolomics* 11, 98-110, doi:10.1007/s11306-014-0676-4 (2015).

(Continued)

*Primary Examiner* — Jay M. Patel
(74) *Attorney, Agent, or Firm* — Sheppard, Mullin, Richter & Hampton LLP

(57) ABSTRACT

Disclosed herein are systems and methods for associating metabolites with genes. In some embodiments, after potential metabolites are identified based on spectroscopy data of the content of an organism, possible reactions capable of producing the potential metabolites are determined. The possible reactions are compared to gene sequences in a database, and an association score for the likelihood that a gene sequence is related to the potential metabolites is calculated.

26 Claims, 10 Drawing Sheets

(56) References Cited

U.S. PATENT DOCUMENTS

| | | | | |
|---|---|---|---|---|
| 6,873,914 | B2* | 3/2005 | Winfield | G16B 50/00 |
| | | | | 702/19 |
| 9,632,999 | B2* | 4/2017 | Azzi | G06F 17/271 |
| 2004/0005612 | A1* | 1/2004 | Giudice | C12Q 1/6883 |
| | | | | 435/6.11 |
| 2004/0044018 | A1* | 3/2004 | Fisher | C07D 471/10 |
| | | | | 514/278 |
| 2007/0061084 | A1* | 3/2007 | Farnet | C12Q 1/02 |
| | | | | 702/19 |
| 2009/0304594 | A1* | 12/2009 | Fantin | A61P 35/00 |
| | | | | 424/9.2 |
| 2010/0116691 | A1* | 5/2010 | Papadimitrakopoulos | |
| | | | | C12Q 1/002 |
| | | | | 205/778 |
| 2015/0160231 | A1* | 6/2015 | Meitei | G01N 33/6851 |
| | | | | 702/22 |
| 2016/0162632 | A1* | 6/2016 | Yun | G16B 5/00 |
| | | | | 506/1 |
| 2018/0095969 | A1* | 4/2018 | Jung | G16B 30/00 |
| 2020/0286580 | A1* | 9/2020 | Chait | C12Q 3/00 |
| 2022/0005552 | A1* | 1/2022 | Galkin | G16H 50/30 |

OTHER PUBLICATIONS

Alvarez, M. A., Fu, H., Khosla, C., Hopwood, D. A. & Bailey, J. E. Engineered biosynthesis of novel polyketides: Properties of the whiE aromatase/cyclase. *Nature Biotechnology* 14, 335-338, doi:DOI 10.1038/nbt0396-335 (1996).

Ames, B. D. et al. Crystal structure and functional analysis of tetracenomycin ARO/CYC: Implications for cyclization specificity of aromatic polyketides. *Proceedings of the National Academy of Sciences of the United States of America* 105, 5349-5354, doi:10.1073/pnas.0709223105 (2008).

Aziz, R. K. et al. The RAST server: Rapid annotations using subsystems technology. *Bmc Genomics* 9, doi:Artn 75 10.1186/1471-2164-9-75 (2008).

Bowen, B. P. & Northen, T. R. Dealing with the unknown: metabolomics and metabolite atlases. *J Am Soc Mass Spectrom* 21, 1471-1476, doi:10.1016/j.jasms.2010.04.003 (2010).

Caspi, R. et al. The MetaCyc database of metabolic pathways and enzymes and the BioCyc collection of pathway/genome databases. *Nucleic Acids Research* 44, D471-D480, doi:10.1093/nar/gkv1164 (2016).

Cooper, L. E. et al. In Vitro Reconstitution of the Radical S-Adenosylmethionine Enzyme MqnC Involved in the Biosynthesis of Futalosine-Derived Menaquinone. *Biochemistry* 52, 4592-4594, doi:10.1021/bi400498d (2013).

Craney, A., Ahmed, S. & Nodwell, J. Towards a new science of secondary metabolism. *J Antibiot* 66, 387-400, doi:10.1038/ja.2013.25 (2013).

Creek, D. J. et al. Metabolite identification: are you sure? And how do your peers gauge your confidence? *Metabolomics* 10, 350-353, doi:10.1007/s11306-014-0656-8 (2014).

Dhanasekaran, A. R., Pearson, J. L., Ganesan, B. & Weimer, B. C. Metabolome searcher: a high throughput tool for metabolite identification and metabolic pathway mapping directly from mass spectrometry and using genome restriction. *Bmc Bioinformatics* 16, doi:ARTN 62 10.1186/s12859-015-0462-y (2015).

Duhrkop, K., Shen, H. B., Meusel, M., Rousu, J. & Bocker, S. Searching molecular structure databases with tandem mass spectra using CSI:FingerID. *Proceedings of the National Academy of Sciences of the United States of America* 112, 12580-12585, doi:10.1073/pnas. 1509788112 (2015).

Hadadi, N., Hafner, J., Shajkofci, A., Zisaki, A. & Hatzimanikatis, V. Atlas of Biochemistry: A Repository of All Possible Biochemical Reactions for Synthetic Biology and Metabolic Engineering Studies. *Acs Synthetic Biology* 5, 1155-1166, doi:10.1021/acssynbio.6b00054 (2016).

Hattori, M., Okuno, Y., Goto, S. & Kanehisa, M. Development of a chemical structure comparison method for integrated analysis of chemical and genomic information in the metabolic pathways. *J Am Chem Soc* 125, 11853-11865, doi:10.1021/ja036030u (2003).

Hattori, M., Tanaka, N., Kanehisa, M. & Goto, S. SIMCOMP/SUBCOMP: chemical structure search servers for network analyses. *Nucleic Acids Res* 38, W652-656, doi:10.1093/nar/gkq367 (2010).

Hatzimanikatis, V. et al. Exploring the diversity of complex metabolic networks. *Bioinformatics* 21, 1603-1609, doi:10.1093/bioinformatics/bti213 (2005).

Haynes, S. W., Sydor, P. K., Stanley, A. E., Song, L. J. & Challis, G. L. Role and substrate specificity of the Streptomyces coelicolor RedH enzyme in undecylprodiginine biosynthesis. *Chem Commun*, 1865-1867, doi:10.1039/b801677a (2008).

Hiratsuka, T. et al. An alternative menaquinone biosynthetic pathway operating in microorganisms. *Science* 321, 1670-1673, doi:10.1126/science.1160446 (2008).

Horai, H. et al. MassBank: a public repository for sharing mass spectral data for life sciences. *J Mass Spectrom* 45, 703-714, doi:10.1002/jms.1777 (2010).

Huan, T. et al. Systems biology guided by XCMS Online metabolomics. *Nature Methods* 14, 461-462 (Apr. 2017).

Ichinose, K. et al. Proof that the actVI genetic region of Streptomyces coelicolor A3(2) is involved in stereospecific pyran ring formation in the biosynthesis of actinorhodin. *Bioorganic & Medicinal Chemistry Letters* 9, 395-400, doi:Doi 10.1016/S0960-894x(99)00011-6 (1999).

Johnson, J. W., Fisher, J. F. & Mobashery, S. Bacterial cell-wall recycling. *Ann Ny Acad Sci* 1277, 54-75, doi:10.1111/j.1749-6632.2012.06813.x (2013).

Kanehisa, M., Sato, Y., Kawashima, M., Furumichi, M. & Tanabe, M. Kegg as a reference resource for gene and protein annotation. *Nucleic Acids Research* 44, D457-D462, doi:10.1093/nar/gkv1070 (2016).

Kell, D. B. & Oliver, S. G. The metabolome 18 years on: a concept comes of age. *Metabolomics* 12, doi:ARTN 148 10.1007/s11306-016-1108-4 (2016).

Kendrew, S. G., Hopwood, D. A. & Marsh, E. N. G. Identification of a monooxygenase from Streptomyces coelicolor A3(2) involved in biosynthesis of actinorhodin: Purification and characterization of the recombinant enzyme. *Journal of Bacteriology* 179, 4305-4310 (1997).

Li, C. H. et al. Computational discovery of biochemical routes to specialty chemicals. *Chem Eng Sci* 59, 5051-5060, doi:10.1016/j.ces.2004.09.021 (2004).

Li, S. Z. et al. Predicting Network Activity from High Throughput Metabolomics. *Plos Computational Biology* 9, doi:ARTN e1003123 10.1371/journal.pcbi.1003123 (2013).

Liu, X. J. & Locasale, J. W. Metabolomics: A Primer. *Trends in Biochemical Sciences* 42, 274-284, doi:10.1016/j.tibs.2017.01.004 (Apr. 2017).

Mahanta, N., Fedoseyenko, D., Dairi, T. & Begley, T. P. Menaquinone Biosynthesis: Formation of Aminofutalosine Requires a Unique Radical SAM Enzyme. *Journal of the American Chemical Society* 135, 15318-15321, doi:10.1021/ja408594p (2013).

McDaniel, R., Ebertkhosla, S., Fu, H., Hopwood, D. A. & Khosla, C. Engineered Biosynthesis of Novel Polyketides—Influence of a Downstream Enzyme on the Catalytic Specificity of a Minimal Aromatic Polyketide Synthase. *Proceedings of the National Academy of Sciences of the United States of America* 91, 11542-11546, doi:DOI 10.1073/pnas.91.24.11542 (1994).

Mcdaniel, R., Hutchinson, C. R. & Khosla, C. Engineered Biosynthesis of Novel Polyketides—Analysis of Tcmn Function in Tetracenomycin Biosynthesis. *Journal of the American Chemical Society* 117, 6805-6810, doi:DOI 10.1021/ja00131a001 (1995).

Morgat, A. et al. Updates in Rhea—an expert curated resource of biochemical reactions. *Nucleic Acids Research* 45, D415-D418, doi:10.1093/nar/gkw990 (Jan. 2017).

Moriya, Y., Itoh, M., Okuda, S., Yoshizawa, A. C. & Kanehisa, M. Kaas: an automatic genome annotation and pathway reconstruction server. *Nucleic Acids Res* 35, W182-185, doi:10.1093/nar/gkm321 (2007).

(56) References Cited

OTHER PUBLICATIONS

Nowicka, B. & Kruk, J. Occurrence, biosynthesis and function of isoprenoid quinones. *Bba-Bioenergetics* 1797, 1587-1605, doi:10.1016/j.bbabio.2010.06.007 (2010).

Oellien, F., Cramer, J., Beyer, C., Ihlenfeldt, W. D. & Selzer, P. M. The impact of tautomerforms on pharmacophore-based virtual screening. *J Chem Inf Model* 46, 2342-2354, doi:10.1021/ci060109b (2006).

Park, J. T. & Uehara, T. How bacteria consume their own exoskeletons (Turnover and recycling of cell wall peptidoglycan). *Microbiology and Molecular Biology Reviews* 72, 211-227, doi:10.1128/Mmbr.00027-07 (2008).

Pluskal, T., Castillo, S., Villar-Briones, A. & Oresic, M. MZmine 2: modular framework for processing, visualizing, and analyzing mass spectrometry-based molecular profile data. *BMC Bioinformatics* 11, 395, doi: 10.1186/1471-2105-11-395 (2010).

Ridder, L. et al. Automatic Chemical Structure Annotation of an LC-MSn Based Metabolic Profile from Green Tea. *Analytical Chemistry* 85, 6033-6040, doi:10.1021/ac400861a (2013).

Saito, K. & Matsuda, F. Metabolomics for Functional Genomics, Systems Biology, and Biotechnology. *Annu Rev Plant Biol* 61, 463-489, doi: 10.1146/annurev.arplant.043008.092035 (2010).

Schnoes, A. M., Brown, S. D., Dodevski, I. & Babbitt, P. C. Annotation Error in Public Databases: Misannotation of Molecular Function in Enzyme Superfamilies. *Plos Computational Biology* 5, doi:ARTN e1000605 10.1371/journal.pcbi.1000605 (2009).

Shen, Y. M. et al. Ectopic expression of the minimal whiE polyketide synthase generates a library of aromatic polyketides of diverse sizes and shapes. *Proceedings of the National Academy of Sciences of the United States of America* 96, 3622-3627, doi:DOI 10.1073/pnas.96.7.3622 (1999).

Smith, C. A. et al. METLIN: a metabolite mass spectral database. *Ther Drug Monit* 27, 747-751 (2005).

Taguchi, T. et al. Chemical characterisation of disruptants of the Streptomyces coelicolor A3(2) actVI genes involved in actinorhodin biosynthesis. *J Antibiot* 53, 144-152 (2000).

Temperton, B. & Giovannoni, S. J. Metagenomics: microbial diversity through a scratched lens. *Curr Opin Microbiol* 15, 605-612, doi:10.1016/j.mib.2012.07.001 (2012).

Valton, J., Filisetti, L., Fontecave, M. & Niviere, V. A two-component flavin-dependent monooxygenase involved in actinorhodin biosynthesis in Streptomyces coelicolor. *Journal of Biological Chemistry* 279, 44362-44369, doi:10.1074/jbc.M407722200 (2004).

Vaniya, A. & Fiehn, O. Using fragmentation trees and mass spectral trees for identifying unknown compounds in metabolomics. *Trac-Trend Anal Chem* 69, 52-61, doi:10.1016/j.trac.2015.04.002 (2015).

Wang, Y., Kora, G., Bowen, B. P. & Pan, C. MIDAS: a database-searching algorithm for metabolite identification in metabolomics. *Anal Chem* 86, 9496-9503, doi:10.1021/ac5014783 (2014).

Wolf, S., Schmidt, S., Muller-Hannemann, M. & Neumann, S. In silico fragmentation for computer assisted identification of metabolite mass spectra. *BMC Bioinformatics* 11, 148, doi:10.1186/1471-2105-11-148 (2010).

Wolfender, J. L., Marti, G., Thomas, A. & Bertrand, S. Current approaches and challenges for the metabolite profiling of complex natural extracts. *J Chromatogr A* 1382, 136-164, doi:10.1016/j.chroma.2014.10.091 (2015).

Wu, C. H., Huang, H. Z., Yeh, L. S. L. & Barker, W. C. Protein family classification and functional annotation. *Comput Biol Chem* 27, 37-47, doi: 10.1016/S1476-9271(02)00098-1 (2003).

Yang, J. Y. et al. Molecular Networking as a Dereplication Strategy. *J Nat Prod* 76, 1686-1699, doi: 10.1021/np400413s (2013).

Yu, T. W. et al. Engineered biosynthesis of novel polyketides from Streptomyces spore pigment polyketide synthases. *Journal of the American Chemical Society* 120, 7749-7759, doi:DOI 10.1021/ja9803658 (1998).

Zampieri, M., Sekar, K., Zamboni, N. & Sauer, U. Frontiers of high-throughput metabolomics. *Current Opinion in Chemical Biology* 36, 15-23, doi:10.1016/j.cbpa.2016.12.006 (Feb. 2017).

* cited by examiner

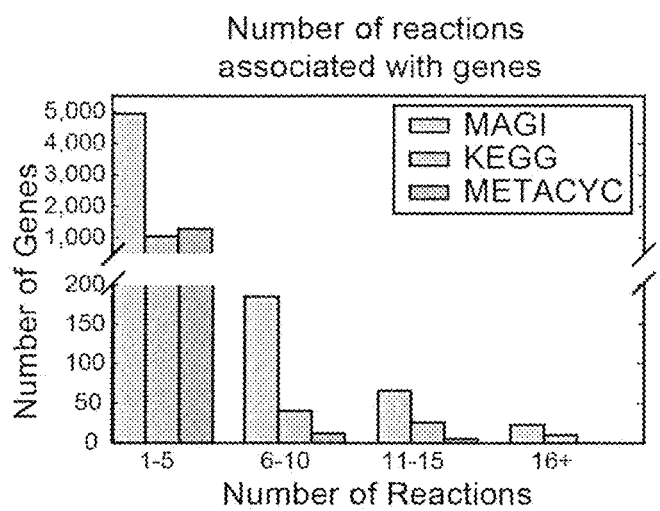
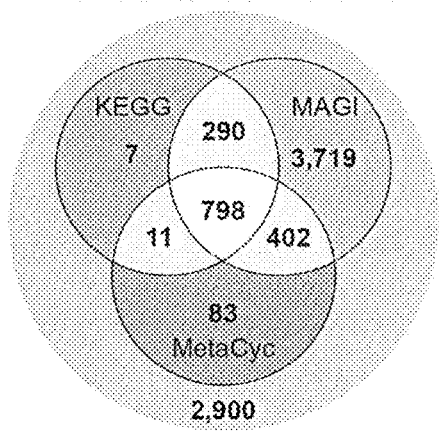
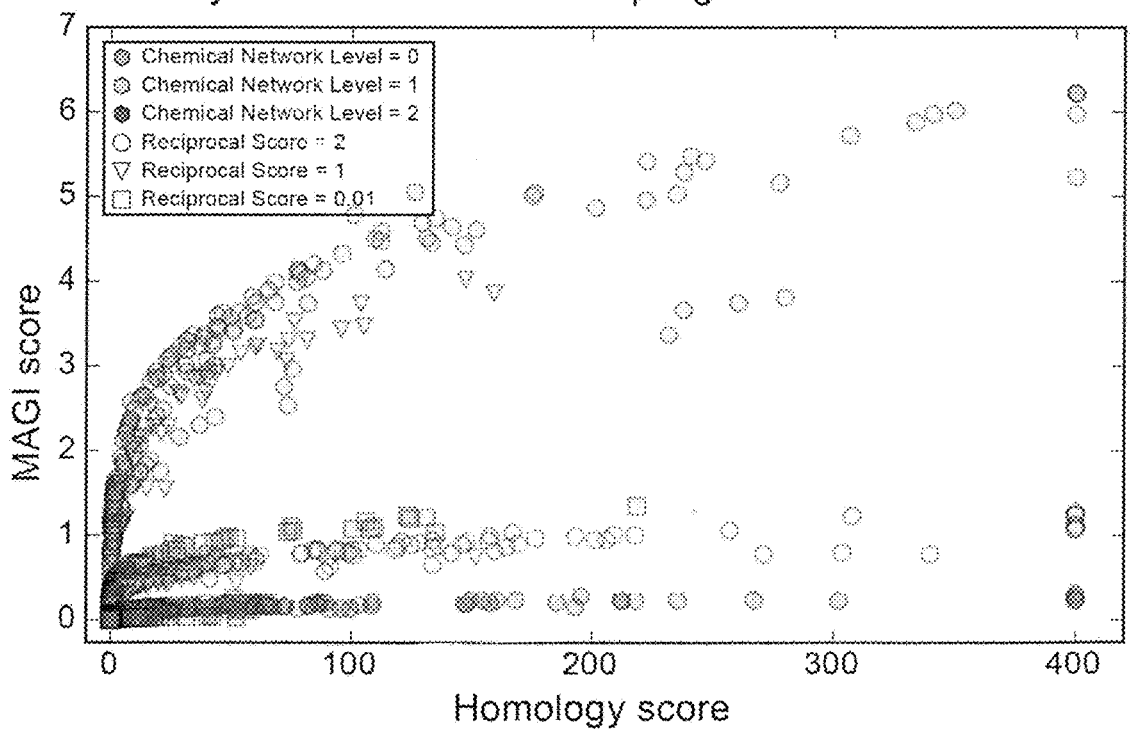
FIG. 6C

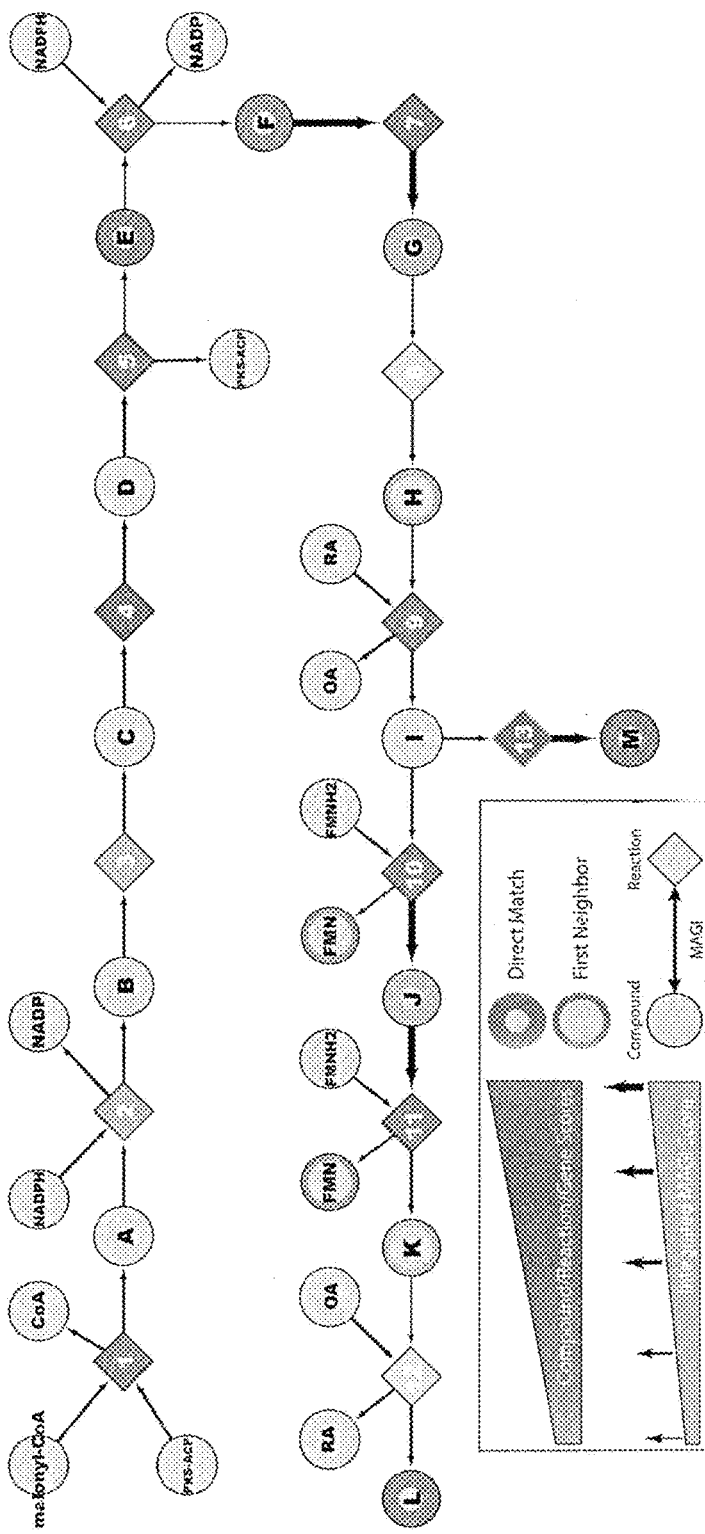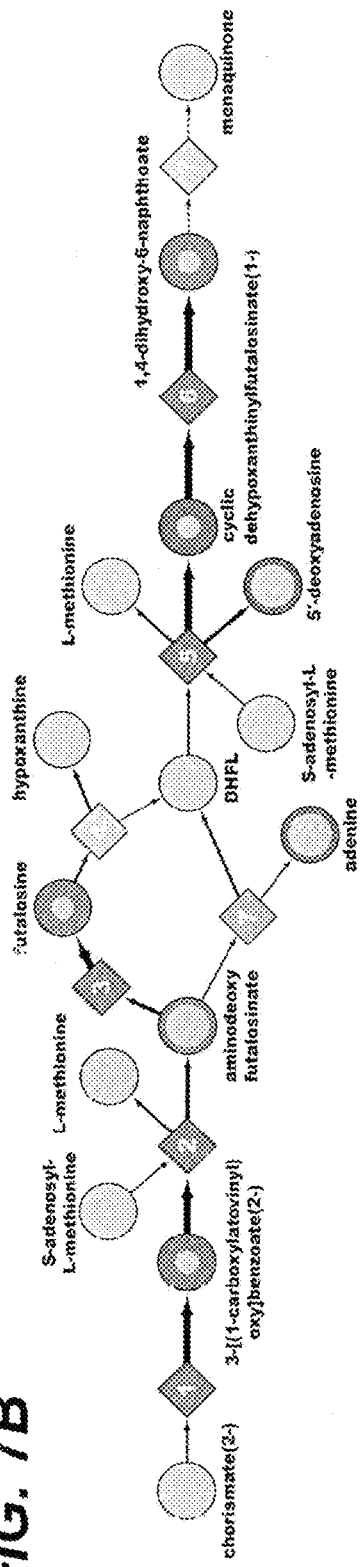
FIG. 7A
FIG. 7B

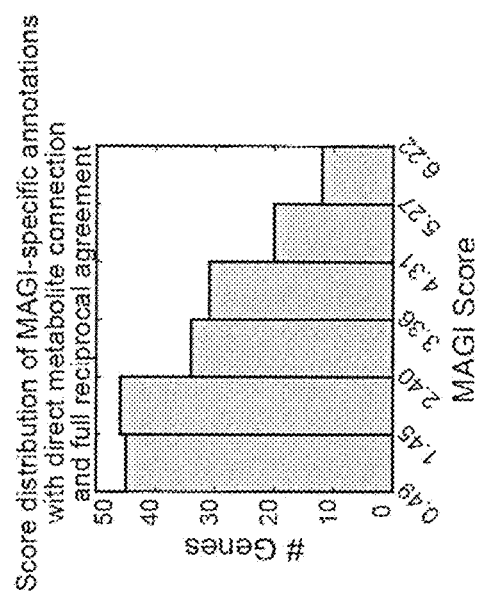
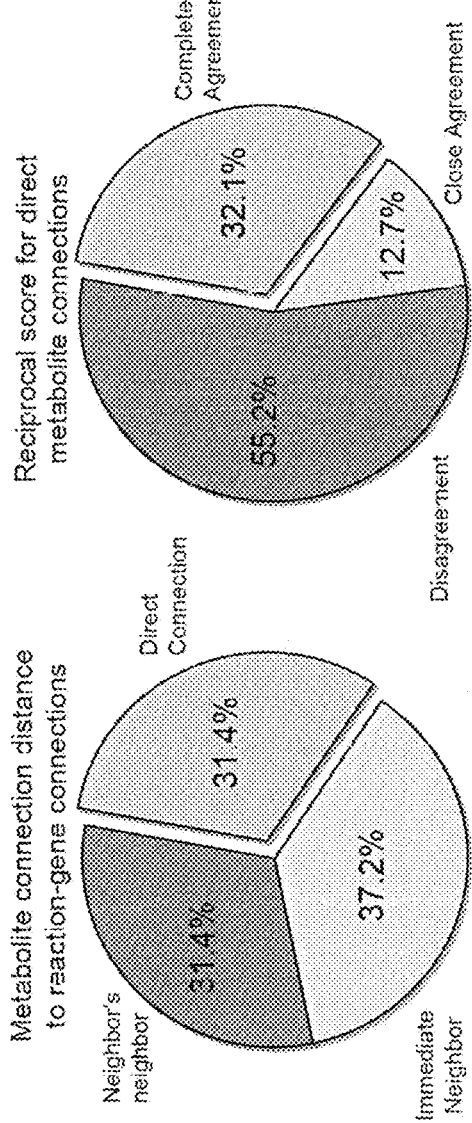
FIG. 9C
FIG. 9B
FIG. 9A

METABOLITE, ANNOTATION, AND GENE INTEGRATION SYSTEM AND METHOD

RELATED APPLICATIONS

The present application claims priority under 35 U.S.C. § 119(e) to U.S. Provisional Application No. 62/460,680, filed on Feb. 17, 2017; and U.S. Provisional Application No. 62/578,956, filed on Oct. 30, 2017. The content of each of these related applications is incorporated herein by reference in its entirety.

STATEMENT REGARDING FEDERALLY SPONSORED R&D

This invention was made with government support under grant No. DE-ACO2-05CH11231 awarded by the U.S. Department of Energy. The government has certain rights in the invention.

FIELD

The present disclosure relates generally to the field of multiomics and more particularly to identifying associations between metabolites and genes.

DESCRIPTION OF THE RELATED ART

Metabolomics has been used for obtaining direct measures of metabolic activities from diverse biological systems. However, metabolomics can be limited by ambiguous metabolite identifications. Furthermore, interpretation can be limited by incomplete and inaccurate genome-based predictions of enzyme activities (e.g., gene annotations). In addition, some genes may be poorly annotated. Thus, the understanding of metabolism, such as microbial metabolism, is limited.

SUMMARY

Disclosed herein are systems and methods for associating metabolites with genes. In one example, a system includes: a non-transitory memory configured to store executable instructions; and a hardware processor in communication with the non-transitory memory, the hardware processor programmed by executable instructions to: receive metabolite spectroscopy data of the content of an organism; identify a plurality of first potential metabolites based on the spectroscopy data; determine a plurality of first possible reactions capable of producing the first potential metabolites; compare the first possible reactions to a database of gene sequences; and determine an association score for the likelihood that a gene sequence is related to the first potential metabolites.

Another example is a method that includes: receiving liquid chromatography mass spectrometry (LCMS) data of a sample comprising a plurality of metabolites of an organism; determining one or more of a metabolite score, a homology score, a reciprocal agreement score, and an aggregate score for each of a plurality of metabolite-reaction-gene associations based on the LCMS data; and performing an analysis of the metabolite score, the homology score, the reciprocal agreement score or the aggregate score to determine an association between the metabolite and the gene.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 6A-6C show MAGI associates more genes with reactions that can be ranked in *S. coelicolor*. FIG. 6A is a bar chart showing the number of reactions associated with each gene by MAGI, KEGG, and BioCyc. FIG. 6C is a Venn diagram showing the genes connected to one or more reactions by MAGI, KEGG, and/or BioCyc. FIG. 6C is a scatter plot of the top MAGI score for each gene that was not connected with a reaction by KEGG or BioCyc, but was associated with one or more metabolites by MAGI, broken down by distance traveled in the chemical network (colors), where teal is a direct metabolite match (i.e. the network was not used), and by reciprocal agreement of the reaction-to-gene and gene-to-reaction searches in MAGI (shapes). The teal circles are the strongest metabolite-reaction connections. For further explanation of individual scores, see Methods.

FIGS. 7A-7B show pathway views of MAGI results. Metabolite, homology, and integrative MAGI scores throughout the actinorhodin (FIG. 7A) and menaquinone (FIG. 7B) biosynthesis pathway guides MAGI interpretations by visualizing results in a broader context. Circular nodes represent metabolites, diamond nodes represent reactions, and edges represent MAGI consensus scores. Border color of circular nodes corresponds to the MIDAS metabolite score, and border width corresponds to the chemical network level searched in MAUI. Fill color of diamond nodes correspond to the homology score. The line width of the edges corresponds to the MAGI score. Abbreviations and legends for metabolites and reactions are in Tables 9A and 9B. The final step(s) in the menaquinone biosynthesis are currently not known and are represented by dashed edges and a "?" as the reaction.

Undecylprodigiosin was queried for similar metabolites in the chemical network, finding prodigiosin, which is in the prodigiosin synthase reaction. This reaction does have a reference sequence, which was used in a homology search against the *S. coelicolor* genome (Reaction to Gene BLAST), finding SCO5896 as the top hit. In the lower half of the flowchart, the SCO5896 gene sequence was queried against the entire MAGI reaction reference sequence database in a homology search (Gene to Reaction BLAST), finding the prodigiosin synthase and norprodigiosin synthase reactions. Norprodigiosin synthase did not have any metabolomics evidence. The metabolite-to-reaction and gene-to-reaction results were connected via the shared prodigiosin synthase reaction, effectively linking the feature 392.2720 to undecylprodigiosin and to SCO5896.

FIGS. 9A-9C are charts demonstrating Prioritization of MAGI gene function suggestions. FIG. 9A is a pie chart showing that of the 1,883 magi-specific gene-metabolite linkages (FIG. 6C), 591 genes were associated with a reaction that was directly connected to an observed metabolite (i.e. the chemical similarity network was not used to link a metabolite to the reaction) (light blue). FIG. 9B is a pie chart showing that of those, 190 genes had reciprocal agreement in bidirectional BLAST searches (light blue). FIG. 9C is a histogram of the top MAGI scores of the 190 genes from FIG. 9B.

Figure 10:
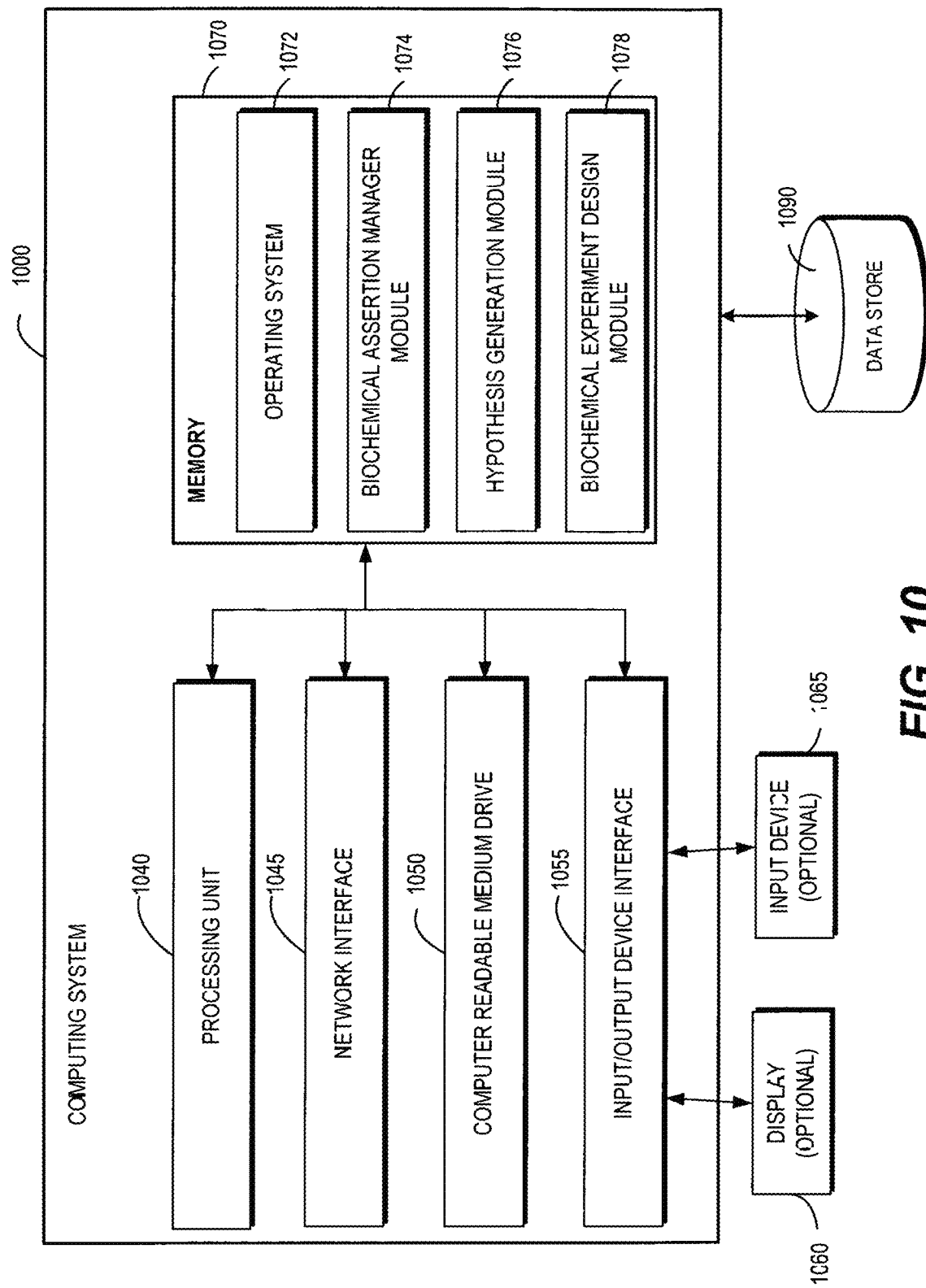

FIG. 10 is a block diagram of an illustrative computing system configured to implement the MAGI workflow.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989).

Overview

Existing methods may require accessing a multitude of disconnected websites and resources to connect a gene sequence to a compound in a reaction. The sequence databases used may dramatically affect the results obtained. Existing methods may annotate genes by comparing the gene sequence to large databases with vast amounts of inaccurate and/or incorrect sequence annotations with little or no experimental evidence. Existing methods may require searching with multiple synonyms or structures of reactions to ensure any reactions involving a compound are not missed. The reference sequences for those reactions may have to be manually collected before homology searching is conducted.

Embodiments disclosed herein include systems and methods for effectively connecting metabolomics data with genomics data using a Bayesian-like process, which can help to ease the problem of compound identification in mass spectrometry as well as provide experimental data for gene annotations. Metabolite identification is a major challenge in metabolomics. The Metabolite Annotation, and Gene Integration (MAGI) system may help addresses this challenge by using a novel chemical similarity network and a Bayesian-like method for scoring probable metabolite identifications and probable gene annotations.

The systems and methods disclosed herein can enable scoring and curating compound identities based on their biological relevance, and/or using compound identities from those tools to connect to genes in their biological samples and potentially formulate hypotheses of gene function. Such results can be used to direct high-throughput biochemical assays to greatly reduce biochemical search space. This allows the MAGI system to be a powerful compliment to other assays, such as those described by Sévin et. al. (Nontargeted in vitro metabolomics for high-throughput identification of novel enzymes in *Escherichia coli*, Nature Methods 14, 187-194 (2017), the content of which is incorporated herein by reference in its entirety). Sevin et. al. conducted over 14,000 experimental assays on nearly 1,500 gene products, and obtained functional evidence for 241 of them, biochemically validating 12.

The MAGI systems and methods are highly relevant to and useful in the fields of genomics, metabolomics, and systems biology. Furthermore, as metabolomics data become more widely available for sequenced organisms, MAGI has the potential to improve the understanding of microbial metabolism, while also providing testable hypotheses for specific biochemical functions.

Disclosed herein are systems and methods for accelerating biological engineering and discovery through Metabolite Annotation, and Gene Integration (MAGI). The systems and methods described below may be used to integrate and link multiple types of information, such as information on metabolites, genes, and annotations. In one embodiment, the metabolite, annotation and gene integration system can integrate experimental metabolomics and genomics data with chemical, biochemical, and genomic data to produce and test hypotheses. The metabolomics and genomics data integrated can be, for example, transcriptomics or proteomics datasets, gene overexpression libraries, transposon insertion libraries, CRISPR-associated system (CAS)-mediated gene silencing, or other gene silencing methods. The metabolomics data can be generated using methods such as liquid chromatography-mass spectrometry (LCMS), Matrix-assisted laser desorption/ionization (MALDI) MS, Nanostructure-Initiator Mass Spectrometry (NIMS), gas chromatography MS (GCMS), nuclear magnetic resonance (NMR) spectroscopy, or other methods for measuring the presence of molecules. The genomic sequences can be obtained from repositories or collected de novo using a variety of sequencing approaches, for example, single molecule real time sequencing (available from Pacific Biosciences (Menlo Park Calif.)), Sanger, Sequencing by Synthesis (e.g., available from Illumina (San Diego, Calif.)), and Nanopore. The chemical, biochemical, expression, presence/absence and genomic data may be publicly available. The system is capable of determining connections between chemicals and genes via probabilistic relationships between reactions. For example, the probabilistic relationships can be determined using a chemical similarity network of the present disclosure and protein homology and domain searching. These connections between chemicals and genes can enable the direct testing of specific reactions. The chemical similarity network may include similarity scores between chemicals. For example, two chemicals (e.g., fluoromethane and chloromethane) that differ from each other by one functional group may have a high similarity score. Two chemicals with diverse chemical properties (e.g., a hydrophobic chemical and a hydrophilic chemical) may have a low similarity score.

In one embodiment, the MAGI system can integrate information on chemical reactions, reference genes for those reactions, metadata about the reactions, a matrix of chemical compounds networked by various chemical distances, and analytical chemistry data collected on chemical compounds. The information can be stored in or retrieved from one or more databases, such as the MetaCyc Metabolic Pathway Database (metacyc.org) and the BRENDA enzyme database (brenda-enzymes.org). A chemical similarity network may include the matrix of chemical compounds networked by various chemical distances.

Metabolite, Annotation and Gene Integration System

Figure 1:
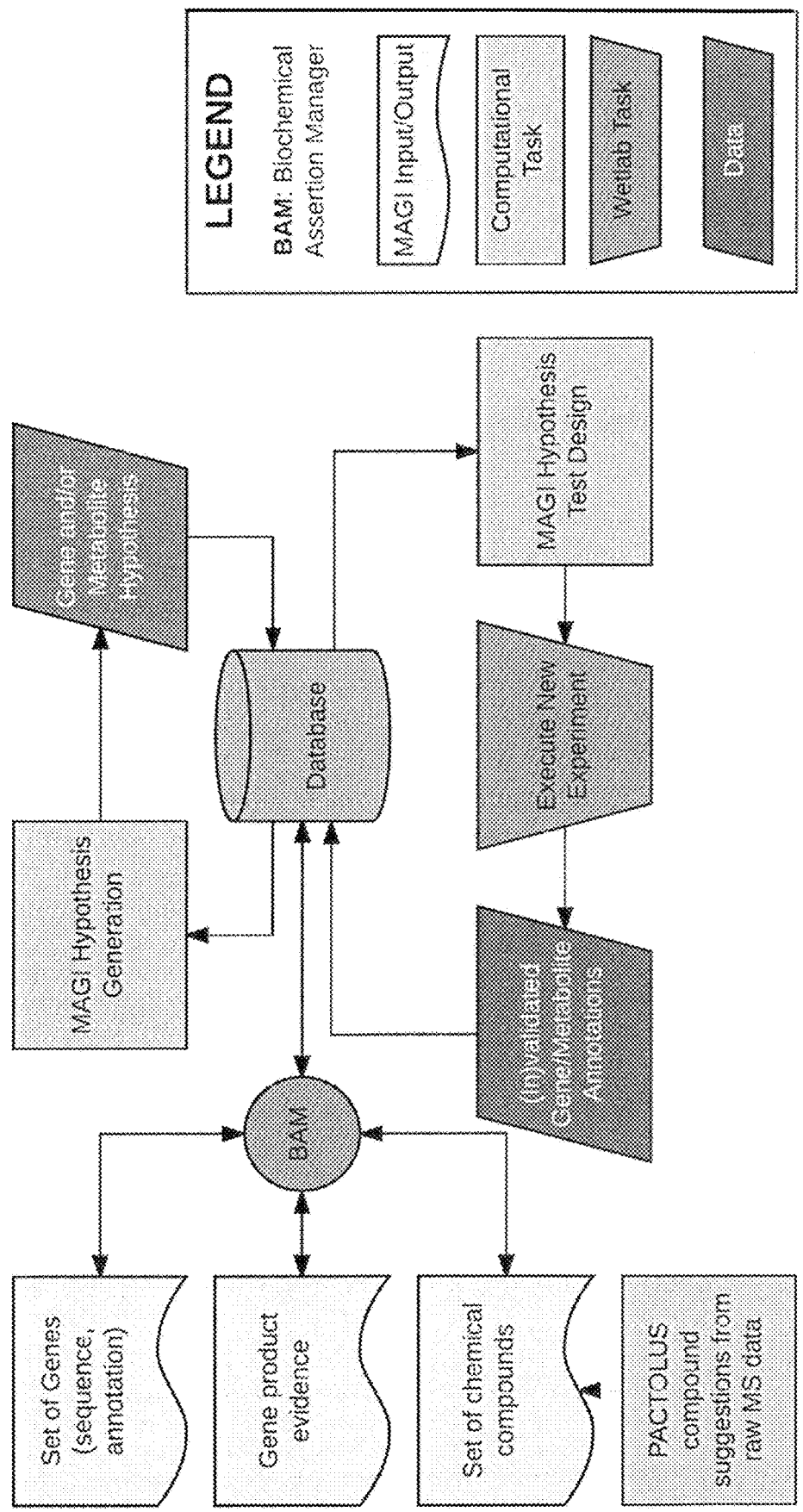
FIG. 1 is a schematic illustration showing a Metabolite Annotation, and Gene Integration (MAGI) workflow.

FIG. 1 is a schematic illustration of a metabolite, annotation and gene integration (MAGI) system. As illustrated in FIG. 1, a biochemical assertion manager (BAM) can organize experimental data inputs for storage in a database. The experimental data inputs can include a set of genes with sequence and annotation, reaction evidence (such as information on chemical reactions), gene product evidence (such as the overexpression, deletion, or silencing of a gene, or proteomics or transcriptomics data), and a set of chemical compounds. The biochemical assertion manager can facilitate the storage of a set of genes with sequence annotation, gene product evidence, and a set of chemical compounds in the database. In one implementation, if the set of the chemical compounds is a result of a mass spectrometry experiment, a list of possible compounds for each mass spectrometry feature can be first calculated and enumerated by Pactolus based on predicted and experimental analytical chemistry data. In one implementation, the biochemical assertion manager can extract results from the database to generate reports. The database can be a custom built, highly organized database that prevents the duplication of sequences, compounds, and reactions, and stores all experimental assertions, which organically expands the reference sequence and reaction library with experimentally validated data, increasing the strength of future assertions over time. The system allows for identification of linkages between sequences and compounds that are not explicitly known and leads to increased reliability of gene function predictions even when homology scores are low.

In one embodiment, the set of chemical compounds can be obtained using a variety of methods other than the "Pactolus" method. Most commonly, authentic standards are used to build a reference library (e.g., a system specific library or a proprietary library) for identification of metabolites. Likewise, untargeted approaches such as MZMINE and XCMS are also widely used. Pactolus is a refinement of the MIDAS approach (Wang, Y et al, MIDAS: A Database-Searching Algorithm for Metabolite Identification in Metabolomics. Analytical Chemistry 2014; 86(19), 9496-9503, DOI: 10.1021/ac5014783, the content of which is incorporated herein in its entirety). Briefly, Pactolus can facilitate identification of compounds for which fragmentation spectra were collected. Pactolus includes high-performance methods to compute all possible fragmentation paths a molecule can follow to generate fragmentation trees. Based on these fragmentation trees, Pactolus can identify new molecules from raw experimental data. In MIDAS the fragmentation trees are computed on the fly and in Pactolus they are precomputed. Accordingly, large databases of chemical compounds can be searched using large collections of measured fragmentation spectra to rank and identify chemical compounds, e.g., a large-scale search for chemical compounds via real, measured data. Other approaches for generating identifications are available (Vaniya, A, et al., Using Fragmentation Trees and Mass Spectral Trees for Identifying Unknown Compounds in Metabolomics. Trends in analytical chemistry 2015; 69:52-61, the content of which is incorporated herein in its entirety). Metabolite identifications can also be obtained by running authentic standards and comparing their mass, retention time and fragmentation pattern matches to measurements to signals obtained from experimental samples.

The metabolite, annotation, and gene integration system can generate a hypothesis for testing computationally using information in the database. For example, the hypothesis generated can be compound-centric or gene-centric (described in greater detail below with reference to FIGS. 2A-2C and FIG. 3). The hypothesis generated can be stored in the database. Furthermore, the system is capable of designing biochemical experiments to test the hypothesis. After executing the experiments, the system can incorporate the experimental results into the database to improve subsequent analyses (described in greater detail below with reference to FIG. 4). For example, experimental results can validate or invalidate gene or metabolite annotations. The database can be updated to include the annotations, by supplementing or replacing existing annotations in the database.

The compound-centric hypothesis may be used to find diverse enzymes that can produce or utilize a compound of interest for biochemistry studies. The compound-centric workflow may also suggest compound identities of mass spectrometry features for conducting untargeted metabolomics experiments. The gene-centric hypothesis can be used to determine gene annotations genome studies. In some implementations, the MAGI system can generate automated experimental design, often a very time-consuming step of enzymology, for enzymology studies. The system can be used to screen genomes for enzymes that have the potential to be engineered or dropped into a desired biosynthetic pathway. Accordingly, biosynthesis of secondary metabolites can be evaluated efficiently and effectively. The automated experimentation of the system can be used to augment genome annotation pipelines with experimentally validated annotations by, for example, large genomics institutions such as the Joint Genome Institute. As the database of reactions and reference sequences grow, the system and the data generated and stored in the database can be used to develop highly accurate metabolic models that incorporate secondary metabolism, for bioinformatics studies. In some embodiments, the system can process a gene sequence to generate a list of designed experiments.

Compound-Centric Hypothesis Generation

Figure 2:
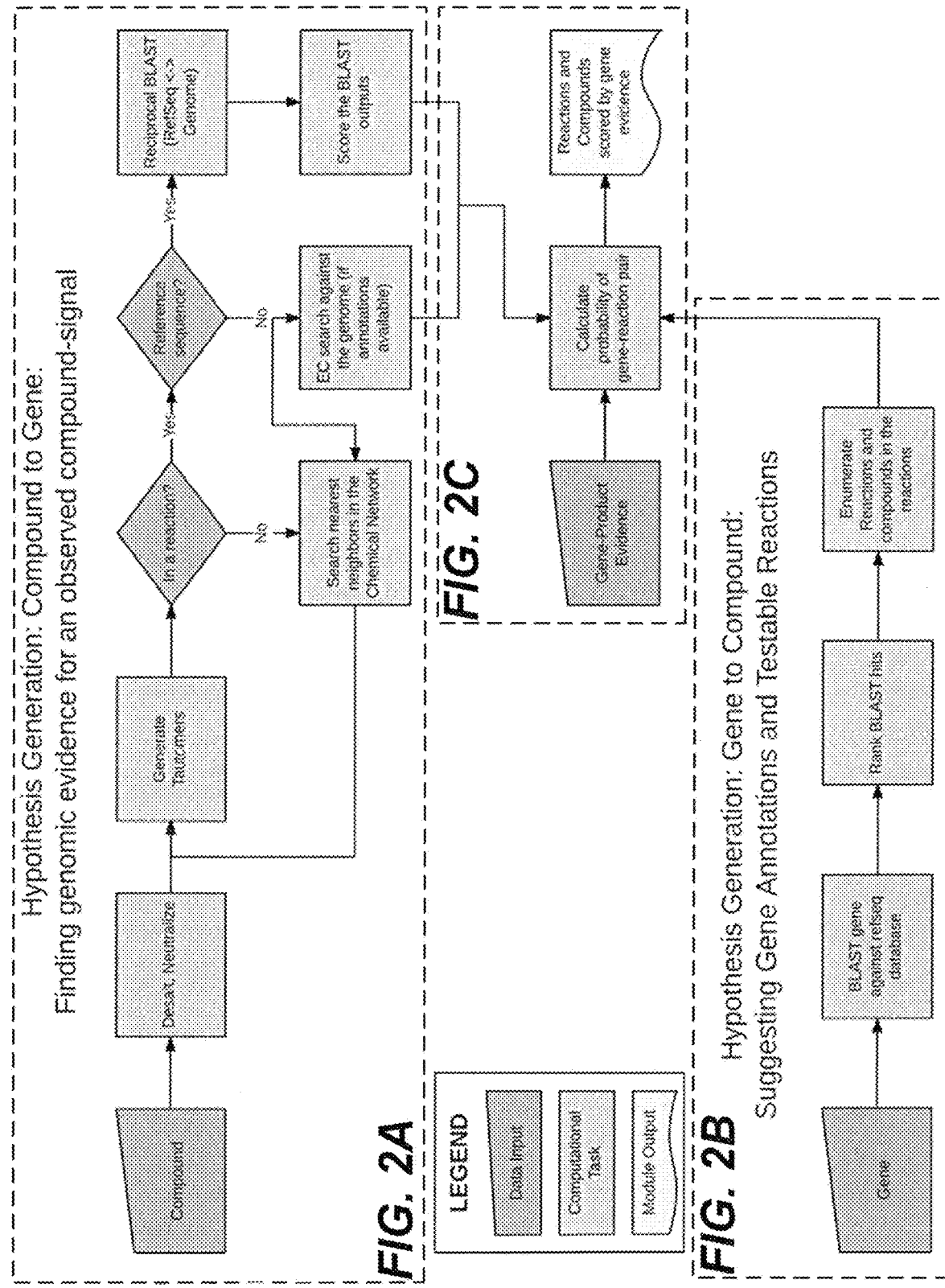
FIGS. 2A-2C show an example hypothesis generation of the MAGI workflow.

FIG. 2A is a schematic illustration of a method for generating a compound-centric hypothesis within a system described herein. The inputs to the compound-centric method can include a list of compounds, a list of genes (e.g. a genome), and optional data files that describe gene annotations or evidence for the presence or absence of a gene product (e.g. proteomics or transcriptomics data). If the compounds are a result of a mass spectrometry experiment, a list of possible compounds for each mass spectrometry feature are first calculated and enumerated by Pactolus based on predicted and experimental analytical chemistry data.

The method can desalt a compound and convert the desalted compound to a neutralized structure in a first step to standardize the molecular structures cheminformatically. In a second standardization step, the method can calculate or enumerate all of the tautomers of the compound. These two steps may improve the accuracy of searching the biochemical reactions because all compounds in the reactions are stored in their desalted and neutralized form, and only one tautomer is chosen to represent a given compound in the reaction. The method can use these tautomers to search the biochemical reactions in the database, generating a complete list of all reactions in which the compound is a product or reactant. Thus, a compound in any format can be converted to a standardized format to search reactions.

In one embodiment, if the compound is not found to be present in any reactions in the database, the method can search the chemical similarity network to find similar compounds that are present in a reaction. If a reaction has a reference sequence associated with it, the method can use all reference sequences in a homology search against the list of genes provided. The method can also perform the reciprocal homology search, where the list of genes is used in a homology search against the complete list of reference sequences, and reciprocal agreement between the two searches is asserted. If the reaction does not have a reference sequence and if gene annotations are provided, the method can use the Enzyme Commission (E.C.) number of the reaction to find genes that are annotated with the same or similar E.C. number. The final output is a list of compounds scored based on how likely the list of gene products is to catalyze reactions in which the compound is involved in, and if the compound is a reactant or product of those reactions.

Figure 3:
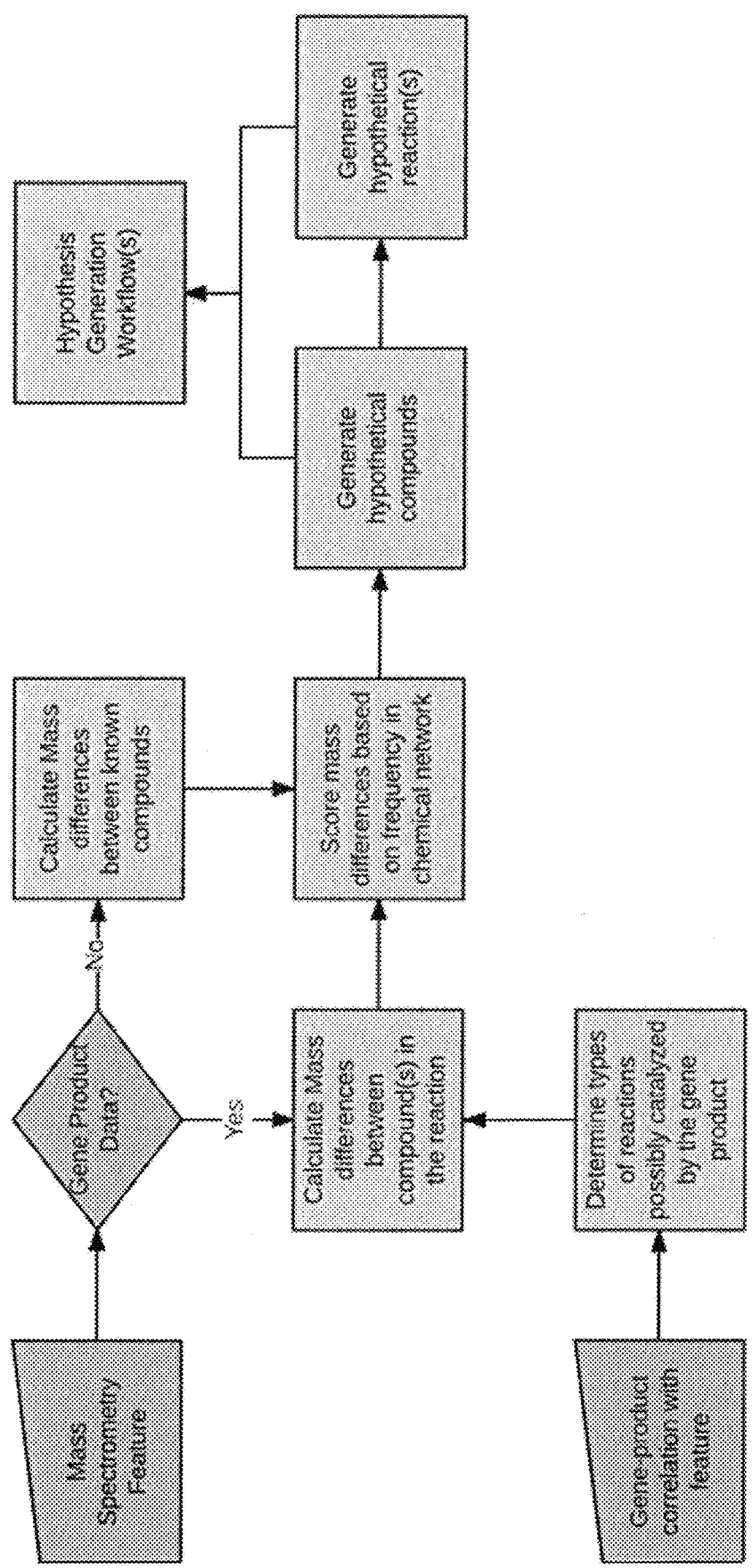
FIG. 3 is a flow diagram showing an example hypothetical compound generation of the MAGI workflow.

FIG. 3 is a schematic illustration of a method for generating assertions about compounds and reactions that are completely novel based on mass spectrometry and gene product evidence (if present). In one embodiment, if a mass spectrometry feature plausibly represents a compound structure not present in the chemical network, the method can generate hypothetical compounds that can represent that feature. These hypothetical compounds can then be substituted for similar compounds in existing reactions, generating hypothetical reactions that can be linked to genes via the same reference sequence to the reaction. The hypothetical compounds and reactions may be integrated with the hypothesis generation workflows.

Gene-Centric Hypothesis Generation

FIG. 2B is a schematic illustration of a method for generating a gene-centric hypothesis within a system described herein. The input to gene-centric hypothesis generation method can include a list of genes (e.g. a genome), and optional data files that may include chemical compounds, gene annotations, and/or evidence for the presence or absence of a gene product (e.g. proteomics or transcriptomics data). The gene-centric hypothesis generation method can perform a reciprocal blast as described above for the compound-centric hypothesis generation method. For example, the gene-centric hypothesis generation method can search reference sequences for homologs in the gene list, and vice versa. The method can rank these homology searches by homology score and reciprocal agreement. For every gene, the method can use the high ranking reference sequence homologs to enumerate biochemical reactions that the gene's product can potentially catalyze. The method can use any additional data to further score the potential of a gene product catalyzing a biochemical reaction. The final output of this method is a ranked list of hypothesized biochemical function(s) for each gene.

Hypothesis Scoring Based on Gene-Product Evidence

FIG. 2C is a schematic illustration of how gene product evidence can be used to further develop and score hypotheses generated by the compound-centric or gene-centric methods. In cases where experimental evidence exists for the presence or absence of a gene (e.g. transcriptomics, proteomics, gene deletions, gene silencing, gene overexpression), these data will be used to further logically rank hypotheses generated by the compound-centric and/or gene-centric methods described above. For example, a wild-type species' data will be compared to a mutant where one gene is deleted. The gene that was deleted may have several viable hypotheses as to its function. However, one compound is no longer detectable in the metabolomics data of the mutant, and all hypotheses relating that compound to the gene will now be scored at a higher likelihood than others. Similar logic will be applied for all experiments where compound levels may correlate with gene product levels.

Biochemical Experiment Design

Figure 4:
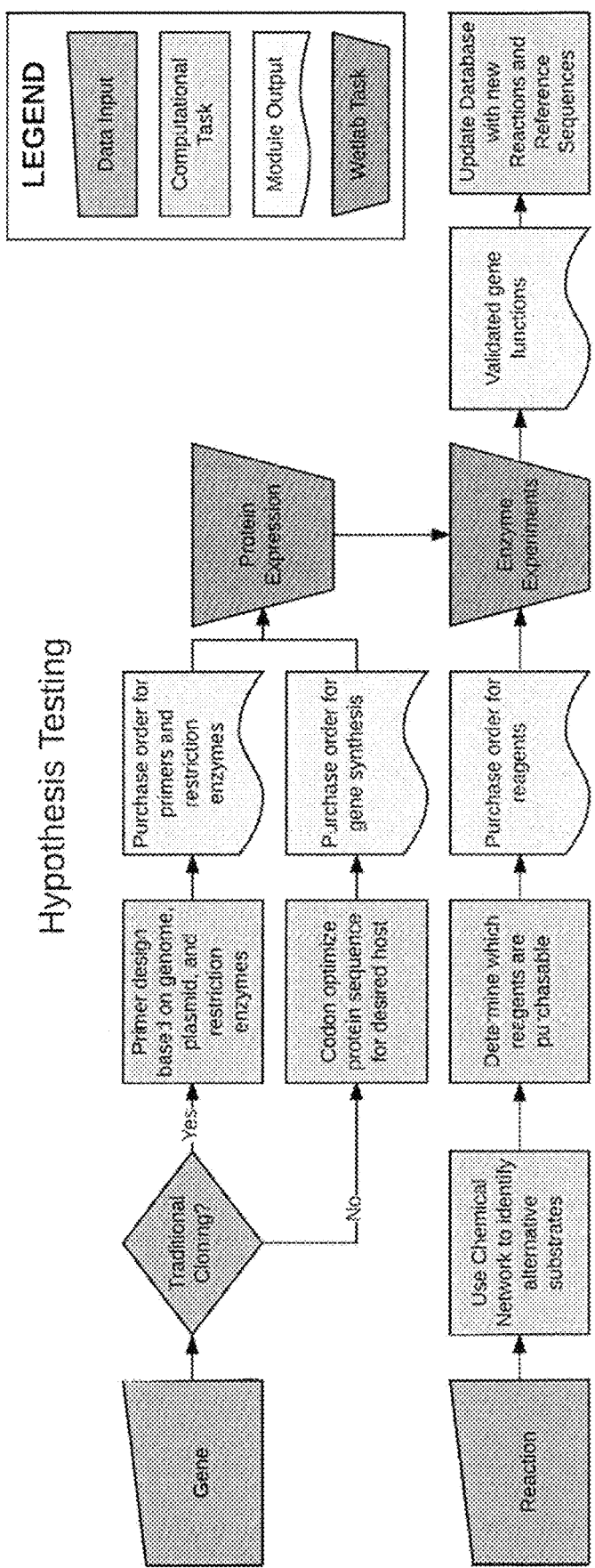
FIG. 4 is a flow diagram showing an example hypothesis testing of the MAGI workflow.

After performing one or both methods of the compound-centric hypothesis and the gene-centric hypothesis generation, the MAGI system can include a biochemical experiment design function that designs biochemical experiments for testing the hypotheses. FIG. 4 is a schematic illustration of a biochemical experiment design method. The inputs to the biochemical experiment generation method include a list of gene-reaction pairs. A gene-reaction pair can be a hypothesis that the gene product catalyzes the reaction.

For each gene, the method can generate one or both of a purchase order for purchasing primers and restriction enzymes to clone the gene into a desired expression vector, and a gene synthesis order for a codon-optimized gene in the desired expression vector. In some implementations, the method can generate, for each reaction, a list of alternative substrates by searching the chemical similarity network for similar reactant and product compounds. The method may not generate false cofactors and coenzymes that would render the reaction impossible. The method can generate a purchase order, based on this list of compounds, for reagents required to validate the hypotheses based on the instrumentation available. The results of the biochemical experiments designed can be incorporated back into the database as experimentally validated assertions.

Once a connection between a gene to a reaction is determined, the method can determine alternative substrates, via the chemical similarity network, for testing in experiments to determine the specific function of an enzyme. Thus, the method can facilitate high throughput testing of substrates to determine the specific function of an enzyme. In one embodiment, the method can identify compounds in untargeted metabolomics experiments. Alternatively or in addition, the method can annotate genes and genomes to reduce improper or incorrect annotations. The method may aide biochemical function discovery, biosynthetic pathway (re)construction, metabolic modeling, and many more aspects of biochemistry. Accordingly, one method, instead of several disconnected methods, can be used to connect a gene to a compound in a reaction, which can in turn be used to determine the gene and metabolite roles. Testing these alternative substrates may be important to determine the specific functional annotation. By testing alternative substrates, the specific type of enzyme encoded by a gene can be determined. For example, the specific type of alcohol dehydrogenase a gene encodes can be determined by testing alternative substrates.

In one implementation, the subsequent protein expression, purification, and enzyme assays can all be miniaturized and/or automated for high-throughput experimentation. Protein expression (e.g., cell-based and cell-free protein expression) and purification systems may be used in multiwall plates, such as 96- or 384-well plates, or in microfluidic droplets. Enzyme reactions can take place in multiwell plates or in barcoded microfluidics droplets. The method can measure the result of the reaction using the Assignment of the Reactions of Gene products in Organisms (ARGO) method for maximum throughput, or other MS or optical methods to determine the progress of a biochemical reaction. By utilizing microfluidics and array-based mass spectrometry technologies, the method can achieve massive throughput in enzyme experiments that can be fully automated.

The ARGO method has been described in U.S. application Ser. No. 15/663,528, filed on Jul. 28, 2017, entitled "METHODS FOR DETERMINING GENE FUNCTIONS," the content of which is hereby incorporated by reference herein in its entirety. Briefly, the ARGO method can be used for determining substrate specificity of an enzyme, identifying an enzyme capable of modifying a substrate of interest, quantifying enzymatic activity, and determining activities of a number of enzymes. For example, the ARGO method can comprise: providing a sample comprising a barcoded enzyme, wherein the barcoded enzyme comprises the enzyme cleavably fused to a barcode (e.g., a peptide barcode); incubating the barcoded enzyme with a protease capable of removing the peptide barcode from the barcoded enzyme and one or more candidate substrates to obtain one or more modified candidate substrates in one or more reactions; generating a mass spectrum of each of the one or more reactions; determining a substrate specificity of the enzyme with respect to each of the one or more candidate substrates based on the mass spectrum; and determining the identity of the barcoded enzyme in the sample by identifying peptide barcode ions in the mass spectrum. As another example, the ARGO method can comprise: providing one or more barcoded enzymes, wherein each of the barcoded enzymes is cleavably fused to a barcode (e.g., a peptide barcode); incubating the one or more barcoded enzymes with a protease capable of removing the peptide barcode from the one or more barcoded enzymes and the substrate of interest to obtain a modified substrate of interest in one or more reactions; generating a mass spectrum of each of the one or more reactions; and determining the activity of each of the one or more barcoded enzymes with respect to the substrate of interest based on the mass spectrum. As yet another example, the ARGO method can comprise: providing one or more barcoded enzymes, wherein each of the one or more barcoded enzymes is cleavably fused to a first peptide barcode; for each of the one or more barcoded enzymes: incubating the barcoded enzyme with a protease capable of removing the peptide barcode from the barcoded enzyme and a candidate substrate to obtain a modified candidate substrate in a reaction; generating a mass spectrum of the reaction; quantifying the barcoded enzyme in the reaction based on the mass spectrum; and quantifying the enzymatic activity of the barcoded enzymes with respect to the candidate substrate based on the ratio of the candidate substrate and the modified candidate substrate in the mass spectrum. As another example, the method can comprise: providing a first barcoded enzyme and a second non-barcoded enzyme, wherein the first barcoded enzyme is cleavably fused to a barcode (e.g., a peptide barcode); incubating the first barcoded enzyme and the second non-barcoded enzyme with a protease capable of removing the peptide barcode from the first barcoded enzyme and one or more candidate substrates to obtain one or more modified candidate substrates in one or more reactions; generating a mass spectrum of each of the one or more reactions; determining the activities of the first barcoded enzyme and the second non-barcoded enzyme with respect to each of the one or more candidate substrates based on the mass spectrum; and determining the identities of the barcoded enzyme and the second non-barcoded enzyme by identifying peptide barcode ions in the mass spectrum.

After the designed biochemical experiments for testing the hypothesis have been performed, the method can update the database with the new reactions and reference sequences to reactions discovered. The new reactions and reference sequences to reactions discovered can supplement or supersede the data in the database used to generate the compound-centric hypothesis or the gene-centric hypothesis, and to design biochemical experiments for hypothesis testing. In some embodiments, the MAGI method can process the original inputs' repeatedly as the database grows, enabling more predictions that are increasingly accurate.

Metabolite, Annotation and Gene Integration

Metabolomics is a widely used technology for obtaining direct measures of metabolic activities from diverse biological systems. However, it is limited by ambiguous metabolite identifications. Furthermore, interpretation is limited by incomplete and inaccurate genome-based predictions of enzyme activities (i.e. gene annotations). Metabolite, Annotation, and Gene Integration (MAGI) addresses these challenges by generating metabolite-gene associations via biochemical reactions based on a score between probable metabolite identifications and probable gene annotations. This is calculated by a Bayesian-like method and emphasizes consensus between metabolites and genes. metabolomics and genomics data by scoring consensus between the two may increase the quality of both metabolite identifications and gene annotations. Moreover, MAGI may make correct biochemical predictions for poorly annotated genes that *can be validated by literature searches. As metabolomics data become more widely available for sequenced organisms, this approach has the potential to improve the understanding of microbial metabolism while also providing testable hypotheses for specific biochemical functions.

Metabolomics approaches now enable global profiling, comparison, and discovery of diverse metabolites present in complex biological samples. Connecting sequence to function by integrating this information with genomic data is one of the most exciting and important applications for metabolomics. The metabolome of a biological system is a direct representation of the biochemical processes that occurred, but accurately associating metabolites and corresponding biochemical reactions with gene products remains challenging.

Liquid chromatography coupled with electrospray ionization mass spectrometry (LCMS) is one of the leading methods in metabolomics. A critical measure in metabolomics datasets is known as a "feature," which is a unique combination of mass-to-charge (m/z) and chromatographic retention time. Each distinct feature may match to hundreds of unique chemical structures. This makes metabolite identification (the accurate assignment of the correct chemical structure to each feature) one of the fundamental challenges in metabolomics. To aid metabolite identification efforts, ions (with a unique m/z and retention time) are typically fragmented, and the resulting fragments are compared against either experimental or computationally predicted reference libraries. While this method is highly effective at reducing the search space for metabolite identification, misidentifications are inevitable, especially for metabolites lacking authentic standards.

One strategy for addressing the large search space of compound identifications is to assess identifications in the context of the predicted metabolism of the organism(s) being studied. Several tools do this with varying degrees of complexity, using strategies that range from mapping metabolites onto reactions to using reaction networks and predictive pathway mapping for scoring the likelihood of metabolite identities. However, many metabolites cannot be included in these approaches due to two major reasons. First, reaction databases lack the majority of known secondary metabolites. Second, gene annotations are incomplete or can be incorrect. Since reactions serve as the pivotal connection between metabolites and genes, these two issues severely limit the integration of metabolomics data with genomic data.

Chemical networking has emerged as a valuable approach to addressing the dearth of metabolites represented in reactions by expanding reaction space based on chemical similarity between metabolites. Effectively, even when a metabolite is not directly involved in a reaction, a linkage can still be made with a reaction based on similarity to another well-studied metabolite. In this way, chemical networking is a viable solution that expands reaction databases to integrate with already expansive metabolite databases. This allows more putative metabolite identifications to be assessed using the predicted metabolism of the organism(s).

The remaining challenge of connecting metabolites with specific gene products is that (like metabolite annotations) gene annotations are also imperfect. This is predominantly due to functional assertions being based on homology to reference sequences unsupported by experimental validation. Annotation services attempt to annotate a gene product with a specific biochemical function, sometimes choosing among equally probable but mutually exclusive functions or leaving them unhelpfully vague. This practice can lead to false conclusions in the absence of biochemical experiments, since some enzymes can have multiple substrates, are multifunctional, or have similar homology to several different reactions. Additionally, some annotations are incorrect due to propagation of false annotations. Conducting one or more metabolomics experiments on a biological system and ultimately linking observed metabolites to gene sequences can provide direct biochemical evidence for a gene product's biochemical function, bolstering existing bioinformatics-based annotations, correcting wrong annotations, and making vague annotations more specific.

Figure 5:
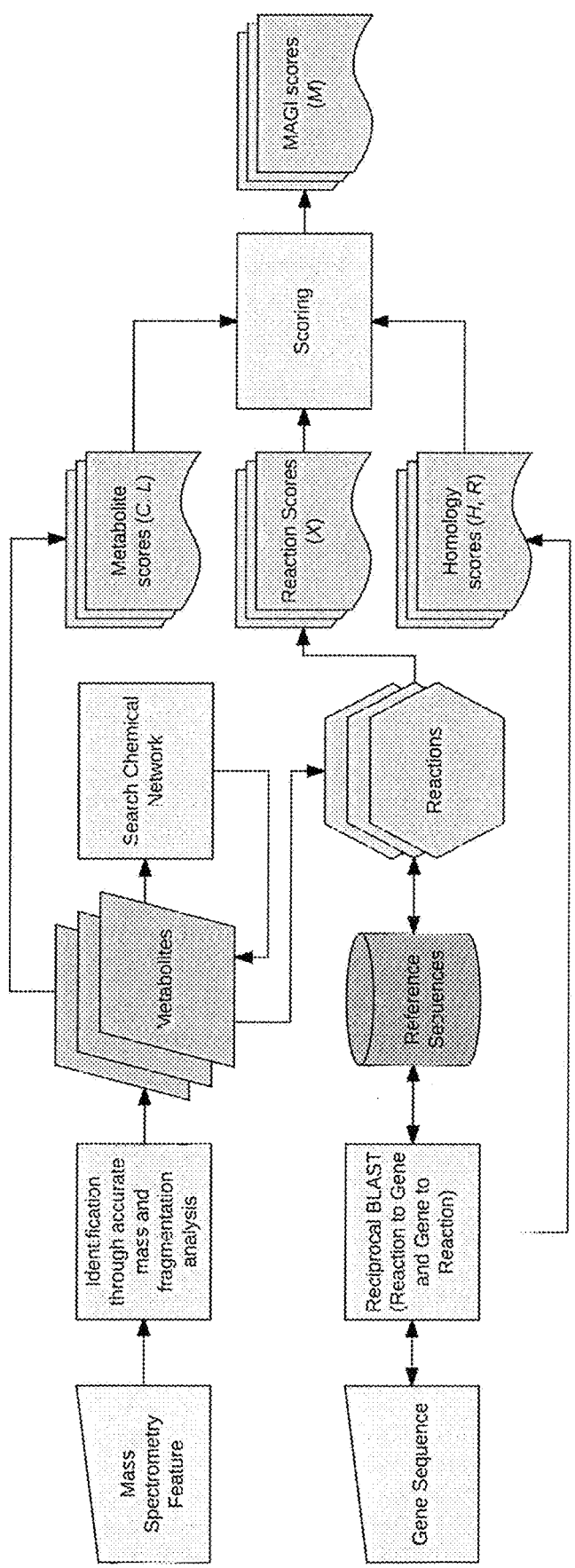
FIG. 5 is a schematic illustration showing a MAGI workflow for consensus scoring. Mass spectrometry features are connected to metabolites via methods such as accurate mass searching or fragmentation pattern matching. These metabolites are expanded to include similar metabolites by using the Chemical Network. These metabolites are then connected to reactions, which are reciprocally linked to input gene sequences via homology (Reciprocal BLAST box). The metabolite, reaction, and homology scores generated throughout the MAGI process are integrated to form MAGI scores (Scoring box). For details on MAGI scores, see Methods.

Disclosed herein is Metabolite, Annotation, and Gene Integration (MAGI), a new tool that generates metabolite-gene associations (FIG. 5). MAGI can quickly find and score consensus between metabolite identifications and gene annotations via a method analogous to Bayesian inference. Essentially, the probability of a metabolite identity increases if there is genetic evidence to support that metabolite, and the probability of a gene function increases if there is metabolomic evidence for that function. Inputs to MAGI can include two datatypes: a metabolite identification file of LCMS features and a protein or gene sequence FASTA file. For each LCMS feature, there are often many plausible metabolite identifications that can be given a probability based on accurate mass error and/or mass fragmentation comparisons. MAGI attempts to link these putative compound identifications to reactions both directly and indirectly by a biochemically relevant chemical similarity network. Likewise, MAGI associates input sequences to biochemical reactions by assessing sequence homology to reference sequences in the MAGI reaction database. For each sequence, there are often several plausible reactions with equal or similar probability. While annotation services would typically reduce specificity in these cases (e.g. simply annotating as oxidoreductase), MAGI keeps all specific reactions as possibilities. Since MAGI comprehensively links both metabolites and sequences to reactions with numerical scores that are proxies for probabilities, a final integrative Bayesian-like MAGI score is calculated that magnifies consensus between a gene annotation and a metabolite identification. In one embodiment, this approach can be applied to one of the best characterized secondary metabolite producing bacteria, Streptomyces coelicolor A3(2), by integrating its genome sequence with untargeted metabolomics data. MAGI may successfully reduce the metabolite identity search space by scoring metabolite identities based on the predicted metabolism of au organism. Additionally, further investigation of the metabolite-gene associations may led to identification of unannotated and misannotated genes that may be subsequently validated using literature searches. These and other examples of MAGI metabolite-reaction-gene associations highlight the key aspects of MAGI.

MAGI workflow. In one embodiment, an input metabolite structure is expanded to similar metabolite structures as suggested by the chemical network and all tautomers of those metabolite. Searching all tautomeric forms of a metabolite structure may enhance metabolite database searches. The reaction database is then queried to find reactions containing these metabolites or their tautomers. Direct matches are stereospecific, but tautomer matches are not. This is due to limitations in the tautomer generating method and in how the chemical network was constructed. The metabolite score, C, is inherited from the MS/MS scoring algorithm and is a proxy for the probability that a metabolite structure is correctly assigned. In our case, it is the MIDAS score, but could be any score due to the using geometric mean to calculate the MAGI score. The metabolite score is set to 1 as a default.

If the reaction has a reference sequence associated with it, this reference sequence is used as a BLAST query against a sequence database of the input gene sequences to find genes that may encode that reaction. The reciprocal BLAST is also performed, where genes in the input gene sequences are queries against the reaction reference sequence database; this finds the reactions that a gene may encode for. In one embodiment, the BLAST results are joined by their common gene sequence and are used to calculate a homology score:

$$H = F + R - |F \cdot R|,$$

where F and R are log-transformed e-values of the BLAST results (a proxy for the probability that two gene sequences are homologs), with F representing the reaction-to-gene BLAST score, and R the gene-to-reaction BLAST score. The homology score is set to 1 if no sequence is matched.

The reciprocal agreement between both BLAST searches is also assessed, namely whether they both agreed on the same reaction or not, formulating a reciprocal agreement score: $\alpha$. $\alpha$ is equal to 2 for reciprocal agreements, 1 for disagreements that had BLAST score within 75% of the larger score, 0.01 for disagreements with very different BLAST scores, and 0.1 for situations where one of the BLAST searches did not yield any results. For cases where metabolites are linked to reactions but there is not a reference protein sequence available, a weight factor, X, is needed. We chose, X, such that when a metabolite is not in any reaction to be 0.01; is in reaction missing a reference sequence to be 1.01; is in a reaction with a sequence to be 2.01.

A final MAGI-score is generated by calculating the geometric mean of the metabolite score, homology score, reciprocal agreement score, and whether or not the metabolite is present in a reaction. The MAGI-score can be Bayesian or Bayesian-like. In one embodiment, the final MAGI-score is calculated as:

$$M = GM([C, H, \alpha, X])/n^L,$$

where M is the MAGI-score (a proxy for the probability that a gene and metabolite are associated), GM represents the function to calculate geometric mean, L is the network level connecting the metabolite to a reaction (a proxy for the probability that a compound is involved in a reaction), and n is a penalty factor for the network level. For example, n may equal to 4, but this parameter may change as the scoring function is optimized and more training data is acquired. Furthermore, weights may be applied to each individual score during the geometric mean calculation to further fine-tune the MAGI scoring process. It is expected these to become optimized as more results are processed through MAGI. Although this was not a formal Bayesian inference, it was Bayesian-like in that all individual scores were proxies to prior probabilities and were integrated at the end of the analysis instead of being used sequentially like in other methods, where a genome is first annotated and then metabolites are "painted" onto that model.

The final output may include a table representing all unique metabolite-reaction-gene associations, their individual scores, and their integrated MAGI score. For scoring metabolite identities, a slice of this final output was created by retaining the top scoring metabolite-reaction-gene association for each unique metabolite structure; these can be mapped back onto the mass spectrometry results table to aid the identification of each mass spectrometry feature. For assessing gene functions, another slice of this final output was created by retaining the top scoring metabolite-reaction-gene association for each unique gene-reaction pair.

Execution Environment

FIG. 10 depicts a general architecture of an example computing device 1000 configured to implement the metabolite, annotation and gene integration system disclosed herein. The general architecture of the computing device 1000 depicted in FIG. 10 includes an arrangement of computer hardware and software components. The computing device 1000 may include many more (or fewer) elements than those shown in FIG. 10. It is not necessary, however, that all of these generally conventional elements be shown in order to provide an enabling disclosure. As illustrated, the computing device 1000 includes a processing unit 1040, a network interface 1045, a computer readable medium drive 1050, an input/output device interface 1055, a display 1060, and an input device 1065, all of which may communicate with one another by way of a communication bus. The network interface 1045 may provide connectivity to one or more networks or computing systems. The processing unit 1040 may thus receive information and instructions from other computing systems or services via a network. The processing unit 1040 may also communicate to and from memory 1070 and further provide output information for an optional display 1060 via the input/output device interface 1055. The input/output device interface 1055 may also accept input from the optional input device 1065, such as a keyboard, mouse, digital pen, microphone, touch screen, gesture recognition system, voice recognition system, gamepad, accelerometer, gyroscope, or other input device.

The memory 1070 may contain computer program instructions (grouped as modules or components in some embodiments) that the processing unit 1040 executes in order to implement one or more embodiments. The memory 1070 generally includes RAM, ROM and/or other persistent, auxiliary or non-transitory computer-readable media. The memory 1070 may store an operating system 1072 that provides computer program instructions for use by the processing unit 1040 in the general administration and operation of the computing device 1000. The memory 1070 may further include computer program instructions and other information for implementing aspects of the present disclosure.

For example, in one embodiment, the memory 1070 includes a biochemical assertion manager 1074 that organizes experimental data inputs for storage in the data store 1090. The memory 1070 may additionally or alternatively include a hypothesis generation module 1076 that generates one or both of compound-centric hypothesis and drug-centric hypothesis. The memory 1070 may additionally or alternatively include a biochemical experiment design module 1078 that design biochemical experiments for testing one or both of compound-centric hypothesis and drug-centric hypothesis generated by the hypothesis generation module 1076 In addition, memory 1070 may include or communicate with the data store 1090 and/or one or more other data stores that store experimental data inputs, the hypotheses generated, and results of the biochemical experiments designed.

The computing device 1000 may be in communication with one or more laboratory instruments for performing the metabolomics and enzymology experiments automatically after the experiments are designed by the biochemical experiment design module 1078. Non-limiting examples of laboratory instruments include a mass spectrometer, a NMR spectrometer, a sample handling instrument (e.g., a liquid-handling robot with microfluidics capabilities). The sample handling instrument can include reagents for performing the experiments designed. The computing device 1000 may control the sample handing instrument to dispense reagents and samples for performing the experiments designed. The computing system 1000 can also control another laboratory instrument (e.g., a mass spectrometer) for analyzing the results of the experiments. In some embodiments, the computing device 1000 and one or more laboratory instruments may form one standalone system. For example, a standalone system can include the computing device 1000, a mass spectrometer, and a liquid-handling robot with microfluidics capabilities.

EXAMPLES

Some aspects of the embodiments discussed above are disclosed in further detail in the following examples, which are not in any way intended to limit the scope of the present disclosure.

Example 1

Metabolite, Annotation, and Gene Integration

MAGI has been applied to data collected from *Streptomyces coelicolor* A3(2), an extensively characterized bacterium that produces diverse secondary metabolites. It was found that coupling metabolomics and genomics data using MAGI increased the quality of both annotations and metabolite identifications. MAGI associated functions with metabolomic evidence to 1,883 previously unannotated genes in *Streptomyces coelicolor* and was found to make correct biochemical predictions for poorly annotated genes. We discuss six examples where MAGI correctly associated gene to function via an observed metabolite (four of which were confirmed by literature searches), where KEGG and/or BioCyc did not annotate the gene at all or had an incorrect annotation.

Methods

Media and culture conditions. A 20 µl, volume of glycerol stock of wild-type *S. coelicolor* spores was cultured in 40 mL R5 medium in a 250-mL flask. One liter of R5 medium base included 103 g sucrose, 0.25 g $K_2SO_4$, 10.12 g $MgCl_2.6H_2O$, 10 g glucose, 0.1 g cas-amino acids, 2 mL trace element solution, 5 g yeast extract, and 5.73 g TES buffer to 1 L distilled water. After autoclave sterilization, 1 mL 0.5% $KH_2PO_4$, 0.4 mL 5M $CaCl_2.2H_2O$, 1.5 mL 20% L-proline, 0.7 ml 1N NaOH were added as per the following protocol: www.elabprotocols.com/protocols/#!protocol=486. Each flask contained a stainless steel spring (McMaster-Carr Supply, part 9663K77), cut to fit in a circle in the bottom of the flask. The spring was used to prevent clumping of *S. coelicolor* during incubation. A foam stopper was used to close each flask (Jaece Industries Inc., Fisher part 14-127-40D). Four replicates of each sample were grown in a 28° C. incubator with shaking at 150 rpm. On day six, 1 mL from each replicate were collected in 2 mL Eppendorf tubes in a sterile hood. Samples were centrifuged at 3,200×g for 8 minutes at 4° C. to pellet the cells. Supernatants were decanted into fresh 2 mL tubes and frozen at −80° C. Pellets were flash frozen on dry ice and then stored at −80° C.

LCMS sample preparation and data acquisition. In preparation for LCMS, medium samples were lyophilized dry. Dried medium was then extracted with 150 µL MeOH containing an internal standard (2-Amino-3-bromo-5-methylbenzoic acid, 1 µg/mL, Sigma, #631531), vortexed, sonicated in a water bath for 10 minutes, centrifuged at 5,000 rpm for 5 min, and supernatant finally centrifuge-filtered through a 0.22 µm PVDF membrane (UFC40GV0S, Millipore). LC-MS/MS was performed on a 2 µL injection, with UHPLC reverse phase chromatography performed using an Agilent 1290 LC stack and Agilent C18 column (ZORBAX Eclipse Plus C18, Rapid Resolution HD, 2.1×50 mm, 1.8 µm) at 60° C. and with MS and MS/MS data collected using a QExactive Orbitrap mass spectrometer (Thermo Scientific, San Jose, Calif.). Chromatography used a flow rate of 0.4 mL/min, first equilibrating the column with 100% buffer A (LC-MS water with 0.1% formic acid) for 1.5 min, then diluting over 7 minutes to 0% buffer A with buffer B (100% acetonitrile with 0.1% formic acid). Full MS spectra were collected at 70,000 resolution from m/z 80-1,200, and MS/MS fragmentation data collected at 17,500 resolution using an average of 10, 20 and 30 eV collision energies.

Feature detection. MZmine (version 2.23) was used to deconvolute mass spectrometry features. The methods and parameters used were as follows (in the order that the methods were applied). MS/MS peaklist builder: retention time between 0.5-13.0 minutes, m/z window of 0.01, time window of 1.00. Peak extender: m/z tolerance 0.01 m/z or 50.0 ppm, min height of 1.0E0. Chromatogram deconvolution: local minimum search algorithm where chromatographic threshold was 1.0%, search minimum in RT range was 0.05 minutes, minimum relative height of 1.0%, minimum absolute height of 1.0E5, minimum ratio of peak top/edge of 1.2, peak duration between 0.01 and 30 minutes. Duplicate peak filter: m/z tolerance of 0.01 m/z or 50.0 ppm, RT tolerance of 0.15 minutes. Isotopic peaks grouper: m/z tolerance of 1.0E-6 m/z or 20.0 ppm, retention time tolerance of 0.01, maximum charge of 2, representative isotope was lowest m/z. Adduct search: RT tolerance of 0.01 minutes, searching for adducts M+Hac-H, M+Cl, with an m/z tolerance of 1.0E-5 m/z or 20.0 ppm and max relative adduct peak height of 1.0%. Join aligner: m/z tolerance of 1.0E-6 m/z or 50.0 ppm, weight for m/z of 5, retention time tolerance of 0.15 minutes, weight for RT of 3. Same RT and m/z range gap filler: m/z tolerance of 1.0E-6 m/z or 20.0 ppm.

Metabolite identification. During the LCMS acquisition, two MS/MS spectra were acquired for every MS spectrum. These MS/MS spectra are acquired using data-dependent criteria in which the 2 most intense ions are pursued for fragmentation, and then the next 2 most intense ions such that no ion is fragmented more frequently than every 10 seconds. To assign probable metabolite identities to a spectrum a modified version of the previously described MIDAS approach was used. Our metabolite database is the merger of HMDB, MetaCyc, ChEB1, WikiData, GNPS, and LipidMaps resulting in approximately 180,000 unique chemical structures. For each of these structures, a comprehensive fragmentation tree was pre-calculated to a depth of 5 bond-breakages; these trees were used to accelerate the MIDAS scoring process. The source code to generate trees and score spectra against trees is available on GitHub (github.com/biorack/pactolus). The following procedure was used in the MIDAS scoring. Precursor m/z values were neutralized by 1.007276 Da. For each metabolite within 10 ppm of the neutralized precursor mass, MS/MS ions were associated with nodes of the fragmentation tree using a window of 0.01 Da using MS/MS neutralizations of 1.00727, 2.01510, and −0.00055, as described. For metabolite-features of interest discussed in the text, retention time, m/z, adduct, and fragmentation pattern were used to define a Metabolite Atlas library (Table 1). For each metabolite, raw data was inspected manually using MZmine to rule out peak misidentifications due to adduct formation and in-source degradation.

TABLE 1

A summary of metabolite atlas of the mass spectrometry features of the disclosure.

| | Label [InChIKey Format] | rt_min | rt_max | rt_peak | mz |
|---|---|---|---|---|---|
| 1 | Dihydrokalafungin; Bicyclic Intermediate E: [ZCJHPTKRISJQTN-SFYZADRCSA-M, | 5.002 | 5.199 | 5.088 | 301.1 |

TABLE 1-continued

| | | | | | |
|---|---|---|---|---|---|
| | PBONQNRANFYEQU-UHFFFAOYSA-M] | | | | |
| 2 | Dihydrokalafungin; Bicyclic Intermediate E: [ZCJHPTKRISJQTN-SFYZADRCSA-M, PBONQNRANFYEQU-UHFFFAOYSA-M] | 4.07 | 4.57 | 4.352 | 301.1 |
| 3 | Dihydrokalafungin; Bicyclic Intermediate E: [ZCJHPTKRISJQTN-SFYZADRCSA-M, PBONQNRANFYEQU-UHFFFAOYSA-M] | 4.81 | 5.007 | 4.896 | 301.1 |
| 4 | Bicyclic Intermediate F; DHKred; (S)-Hemiketal: [XORAIIJQEIRUFP-NSHDSACASA-M, GBBQTBKHHWHZSJ-SFYZADRCSA-M, YIEUIGLDTPWIHC-VQVVDHBBSA-N] | 4.873 | 4.997 | 4.947 | 303.1 |
| 5 | Bicyclic Intermediate F; DHKred; (S)-Hemiketal: [XORAIIJQEIRUFP-NSHDSACASA-M, GBBQTBKHHWHZSJ-SFYZADRCSA-M, YIEUIGLDTPWIHC-VQVVDHBBSA-N] | 4.681 | 4.814 | 4.745 | 303.1 |
| 6 | actinorhodin | 7.509 | 7.778 | 7.568 | 633.1 |
| 7 | anhydro-NAM | 2.295 | 2.455 | 2.362 | 274.1 |
| 8 | carboxyvinyloxy-benzoic acid | 4.608 | 4.808 | 4.702 | 207 |
| 9 | cyclic-DHFL | 2.903 | 3.191 | 3.05 | 293.1 |
| 10 | dihydroxy-naphtoate | 2.924 | 3.166 | 3.074 | 203 |
| 11 | futalosine | 4.114 | 4.28 | 4.163 | 413.1 |
| 12 | undecylprodigiosin | 7.454 | 7.596 | 7.507 | 392.3 |
| 13 | whiE_20C_substrate | 4.555 | 4.881 | 4.711 | 401.1 |

A summary of metabolite atlas of the mass spectrometry features of the disclosure.

| | mz_tolerance | polarity | has_fragmentation_reference | inchi_key | creation_time |
|---|---|---|---|---|---|
| 1 | 10 | negative | FALSE | | |
| 2 | 10 | negative | FALSE | | |
| 3 | 10 | negative | FALSE | | |
| 4 | 10 | negative | FALSE | | |
| 5 | 10 | negative | FALSE | | |
| 6 | 10 | negative | FALSE | VTIKDEXOEJDMJP-WYUUTHIRSA-N | 1466212891 |
| 7 | 10 | negative | FALSE | ZFEGYUMHFZOYIY-MKFCKLDKSA-N | 1466213157 |
| 8 | 10 | negative | FALSE | HGVAHYJMDVROLE-UHFFFAOYSA-N | 1466211838 |
| 9 | 10 | negative | FALSE | BAUPPZJHTWBQAS-ZZWXXDIBSA-N | 1466211442 |
| 10 | 10 | negative | FALSE | HVZYIHBMRFYBRI-UHFFFAOYSA-N | 1466211884 |
| 11 | 10 | negative | FALSE | VEDWXCWBMDQNCV-SCFUHWHPSA-N | 1466212849 |
| 12 | 10 | negative | FALSE | ISFCPXILUVJVOC-KYGJEJSHSA-N | 1466211950 |
| 13 | 10 | negative | FALSE | KQWNMCHCVXVLRS-UHFFFAOYSA-N | 1466212102 |

TABLE 1-continued

|   | synonyms | mono_isotopic_molecular_weight | neutralized_2d_inchi |
|---|---|---|---|
| 1 | | | |
| 2 | | | |
| 3 | | | |
| 4 | | | |
| 5 | | | |
| 6 | actinorhodin | 634.13226 | InChI = 1S/C32H26O14/c1-9-21-15(3-11(45-9)5-19(35)36)29(41)23-17(33)7-13(27(39)25(23)31(21)43)14-8-18(34)24-26(28(14)40)32(44)22-10(2)46-12(6-20(37)38)4-16(22)30(24)42/h7-12, 33-34, 39-40H, 3-6H2, 1-2H3, (H, 35, 36)(H, 37, 38) |
| 7 | 1,6-anhydro-N-acetyl-β-muramate///1,6-anhMurNAc | 275.1005 | InChI = 1S/C11H17NO7/c1-4(10(15)16)18-9-7(12-5(2)13)11-17-3-6(19-11)8(9)14/h4, 6-9, 11, 14H, 3H2, 1-2H3, (H, 12, 13)(H, 15, 16) |
| 8 | 3-[(1-Carboxy-vinyl)oxy]benzoic acid///3-[(1-carboxy-vinyl)oxy]benzoate///16929-37-6///MEGxm0_000050///SCHEMBL11404776///ACon1_000626///CHEBI:77107///3-(1-Carboxy-vinyloxy)benzoic acid///ZINC13435098///3-[(1-Carboxy-ethenyl)oxy]benzoic acid///MCULE-4866422160///NCGG00168900-01///NP-000996///C20772///BRD-K94692633-001-01-9 | 208.03717 | InChI = 1S/C10H8O5/c1-6(9(11)12)15-8-4-2-3-7(5-8)10(13)14/h2-5H, 1H2, (H, 11, 12)(H, 13, 14) |
| 9 | cyclic DHFL///Cyclic de-hypoxanthine futalosine///cyclic dehypoxanthine futalosine///cyclic dehypoxanthinyl-futalosine///(2R,3S,4R)-3,4,5-trihydroxy-4'-oxo-3',4,4',5-tetrahydro-2'H,3H-spiro[furan-2,1'-naphthalene]-6'-carboxylic acid///CHEBI:64252///(1R)-4-Oxo-3'beta,4'beta,5'-trihydroxy-3,4,4',5'-tetrahydro-spiro[naphtalene-1(2H),2'(3'H)-furan]-6-carboxylic acid | 294.07395 | InChI = 1S/C14H14O7/c15-9-3-4-14(11(17)10(16)13(20)21-14)8-2-1-6(12(18)19)5-7(8)9/h1-2, 5, 10-11, 13, 16-17, 20H, 3-4H2, (H, 18, 19) |
| 10 | 5,8-dihydroxy-2-naphthoic acid///1,4-dihydroxy-6-naphthoate///SCHEMBL3389495///1,4-dihydroxy-6-naphthoic | 204.04226 | InChI = 1S/C11H8O4/c12-9-3-4-10(13)8-5-6(11(14)15)1-2-7(8)9/h1-5, 12-13H, (H, 14, 15) |

TABLE 1-continued

| | | | |
|---|---|---|---|
| 11 | futalosine///3-{3-[(2R,3S,4R,5R)-3,4-dihydro-9H-purin-9-yl]tetrahydrofuran-2-yl]propanoyl}benzoic acid///CHEBI:51310///210644-32-9///ZINC38629302///C16999///3-[1,5,6-Trideoxy-1-(1,6-dihydro-6-oxo-9H-purin-9-yl)-|A-D-ribo-heptofuranuronoyl]benzoic Acid | 414.11755 | InChI = 1S/C19H18N4O7/c24-11(9-2-1-3-10(6-9)19(28)29)4-5-12-14(25)15(26)18(30-12)23-8-22-13-16(23)20-7-21-17(13)27/h1-3, 6-8, 12, 14-15, 18, 25-26H, 4-5H2, (H, 28, 29)(H, 20, 21, 27) |
| 12 | undecylprodigiosin///Undecylprodiginine///1H-Pyrrole, 2-((3-methoxy-5-(1H-pyrrol-2-yl)-2H-pyrrol-2-ylidine)methyl)-5-undecyl-///2-((3-Methoxy-5-(1H-pyrrol-2-yl)-2H-pyrrol-2-ylidene)methyl)-5-undecyl-1H-pyrrole///AC1O5PL2///CHEMBL83139///52340-48-4///LS-136987///(2Z,5Z)-3-methoxy-5-pyrrol-2-ylidene-2-[(5-undecyl-1H-pyrrol-2-yl)methylidene]pyrrole | 393.27801 | InChI = 1S/C25H35N3O/c1-3-4-5-6-7-8-9-10-11-13-20-15-16-21(27-20)18-24-25(29-2)19-23(28-24)22-14-12-17-26-22/h12, 14-19, 27-28H, 3-11, 13H2, 1-2H3 |
| 13 | 3,5-dioxo-6-[4,5,7-trihydroxy-3-(3-oxobuta-noyl)naphthalen-2-yl]hexanoate///3,5-dioxo-6-[4,5,7-trihydroxy-3-(3-oxobuta-noyl)naphthalen-2-yl]hexanoix acid | 402.09508 | InChI = 1S/C20H18O9/c1-9(21)2-15(25)18-10(4-12(22)6-14(24)8-17(27)28)3-11-5-13(23)7-16(26)19(11)20(18)29/h3, 5, 7, 23, 26, 29H, 2, 4, 6, 8H2, 1H3, (H, 27, 28) |

| | source | kegg_url | kegg_id | formula | number_components |
|---|---|---|---|---|---|
| 1 | | | | | |
| 2 | | | | | |
| 3 | | | | | |
| 4 | | | | | |
| 5 | | | | | |
| 6 | wikidata///metacyc | www.genome.jp/dbget-bin/www_bget?C06691 | C06691 | C32H26O14 | 1 |
| 7 | metacyc | | | C11H17NO7 | 1 |
| 8 | chebi///metacyc | | | C10H8O5 | 1 |
| 9 | chebi///metacyc | www.genome.jp/dbget-bin/www_bget?C17017 | C17017 | C14H14O7 | 1 |
| 10 | chebi///metacyc | www.genome.jp/dbget-bin/www_bget?C17018 | C17018 | C11H8O4 | 1 |
| 11 | chebi///metacyc | www.genome.jp/dbget-bin/www_bget?C16999 | C16999 | C19H18N4O7 | 1 |
| 12 | | | | C25H35N3O | 1 |
| 13 | metacyc | | | C20H18O9 | 1 |

| | usernam | pubchem_compound_id | metacyc_id | head_id |
|---|---|---|---|---|
| 1 | | | | |
| 2 | | | | |
| 3 | | | | |
| 4 | | | | |
| 5 | | | | |

TABLE 1-continued

| | | | | |
|---|---|---|---|---|
| 6 | bpb | 91819934 | CPD1A0-6123 | 42c6e 100d eb84c 5ea40 2451 5f973 835b |
| 7 | bpd | 90658592 | CPD 0-882 | b617 d4d0 a2df4 141af 0219 3b6a 1c5e7 3 |
| 8 | bpd | 23844017 | CPD-1646 7 | 025e dfdfe 4b04 c079 0b4f9 aa532 3ab2 d |
| 9 | bpd | 44237194 | CPD-1141 9 | c55df 9892 30b4 eb6b 3ba7 050d 2a99f 88 |
| 10 | bpd | 14278030 | CPD-1142 0 | b012 898c 3d71 4549 a5cf5 d8ab 64a4 670 |
| 11 | bpd | 10364451 | CPD-1047 7 | dba3c b66e 54e4 463b bfb70 4d82f f99d4 |
| 12 | bpd | 6438379 | | 8bc4 4999 badb 47d6 976af 3caa8 8784f 1 |
| 13 | bpd | 90659064 | CPD-1664 7 | f6a8b 05b7 6994 7caa8 d5b3 ee9b2 401ef |

| | inchi | neutralized_inchi_key | prev_uid | neutralized_inchi |
|---|---|---|---|---|
| 1 | | | | |
| 2 | | | | |
| 3 | | | | |
| 4 | | | | |
| 5 | | | | |
| 6 | InChI = 1S/C32H26O14/ c1-9-21-15(3-11(45-9)5-19(35)36)29(41)23-17(33)7-13(27(39)25(23)31(21)43)14-8-18(34)24-26(28(14)40)32(44)22-10(2)46-12(6-20(37)38)4-16(22)30(24)42/h7- | VTIKD EXOEJ DMJP-WYUU THIRSA-N | origin | InChI = 1S/C32H26O14/ c1-9-21-15(3-11(45-9)5-19(35)36)29(41)23-17(33)7-13(27(39)25(23)31(21)43)14-8-18(34)24-26(28(14)40)32(44)22-10(2)46-12(6-20(37)38)4-16(22)30(24)42/h7-12, 33-34, 39-40H, 3-6H2, 1-2H3, (H, 35, 36)(H, |

TABLE 1-continued

| | | | | |
|---|---|---|---|---|
| | 12, 33-34, 39-40H, 3-6H2, 1-2H3, (H, 35, 36)(H, 37, 38)/t9-, 10-, 11+, 12+/m1/s1 | | | 37, 38)/t9-, 10-, 11+, 12+/m1/s1 |
| 7 | InChI = 1S/C11H17NO7/c1-4(10(15)16)18-9-7(12-5(2)13)11-17-3-6(19-11)8(9)14/h4, 6-9, 11, 14H, 3H2, 1-2H3, (H, 12, 13)(H, 15, 16)/t4-, 6-, 7-, 8, 9-, 11?/m1/s1 | ZFEGY UMHFZ OYIY-MKFCK LDKSA-N | origin | InChI = 1S/C11H17NO7/c1-4(10(15)16)18-9-7(12-5(2)13)11-17-3-6(19-11)8(9)14/h4, 6-9, 11, 14H, 3H2, 1-2H3, (H, 12, 13)(H, 15, 16)/t4-, 6-, 7-, 8-, 9-, 11?/m1/s1 |
| 8 | InChI = 1S/C10H8O5/c1-6(9(11)12)15-8-4-2-3-7(5-8)10(13)14/h2-5H, 1H2, (H, 11, 12)(H, 13, 14) | HGVAH YJMDV ROLE-UHFFF AOYSA-N | origin | InChI = 1S/C10H8O5/c1-6(9(11)12)15-8-4-2-3-7(5-8)10(13)14/h2-5H, 1H2, (H, 11, 12)(H, 13, 14) |
| 9 | InChI = 1S/C14H14O7/c15-9-3-4-14(11(17)10(16)13(20)21-14)8-2-1-6(12(18)19)5-7(8)9/h1-2, 5, 10-11, 13, 16-17, 20H, 3-4H2, (H, 18, 19)/t10-, 11+, 13?, 14-/m1/s1 | BAUPP ZJHTW BQAS-ZZWXX DIBSA-N | origin | InChI = 1S/C14H14O7/c15-9-3-4-14(11(17)10(16)13(20)21-14)8-2-1-6(12(18)19)5-7(8)9/h1-2, 5, 10-11, 13, 16-17, 20H, 3-4H2, (H, 18, 19)/t10-, 11+, 13?, 14-/m1/s1 |
| 10 | InChI = 1S/C11H8O4/c12-9-3-4-10(13)8-5-6(11(14)15)1-2-7(8)9/h1-5, 12-13H, (H, 14, 15) | HVZYI HBMRF YBRI-UHFFF AOYSA-N | origin | InChI = 1S/C11H8O4/c12-9-3-4-10(13)8-5-6(11(14)15)1-2-7(8)9/h1-5, 12-13H, (H, 14, 15) |
| 11 | InChI = 1S/C19H18N4O7/c24-11(9-2-1-3-10(6-9)19(28)29)4-5-12-14(25)15(26)18(30-12)23-8-22-13-16(23)27/h1-3, 6-18, 12, 14-15, 18, 25-26H, 4-5H2, (H, 28, 29)(H, 20, 21, 27)/t12-, 14-, 15-, 18-/m1/s1 | VEDW XCWB MDQN CV-SCFUH WHPSA-N | origin | InChI = 1S/C19H18N4O7/c24-11(9-2-1-3-10(6-9)19(28)29)4-5-12-14(25)15(26)18(30-12)23-8-22-13-16(23)20-7-21-17(13)27/h1-3, 6-18, 12, 14-15, 18, 25-26H, 4-5H2, (H, 28, 29)(H, 20, 21, 27)/t12-, 15-, 18-/m1/s1 |
| 12 | InChI = 1S/C25H35N3O/c1-3-4-5-6-7-8-9-10-11-13-20-15-16-21(27-20)18-24-25(29-2)19-23(28-24)22-14-12-17-26-22/h12, 14-19, 27-28H, 3-11, 13H2, 1-2H3/b23-22-, 24-18- | ISFCPX ILUVJV OC-KYGJEJ SHSA-N | origin | InChI = 1S/C25H35N3O/c1-3-4-5-6-7-8-9-10-11-13-20-15-16-21(27-20)18-24-25(29-2)19-23(28-24)22-14-12-17-26-22/h12, 14-19, 27-28H, 3-11, 13H2, 1-2H3/b23-22-, 24-18- |
| 13 | InChI = 1S/C20H18O9/c1-9(21)2-15(25)18-10(4-12(22)6-14(24)8-17(27)28)3-11-5-13(23)7-16(26)19(11)20(18)29/h3, 5, 7, 23, 26, 29H, 2, 4, 6, 8H2, 1H3, (H, 27, 28) | KQWN MCHC VXVLR S-UHFFF AOYSA-N | origin | InChI = 1S/C20H18O9/c1-9(21)2-15(25)18-10(4-12(22)6-14(24)8-17(27)28)3-11-5-13(23)7-16(26)19(11)20(18)29/h3, 5, 7, 23, 26, 29H, 2, 4, 6, 8H2, 1H3, (H, 27, 28) |

| | name | neutralized_2d_inchi_key | last_modified | pubchem_url |
|---|---|---|---|---|
| 1 | | | | |
| 2 | | | | |
| 3 | | | | |
| 4 | | | | |
| 5 | | | | |
| 6 | actinorhodin// Actinorhodin | VTIKD EXOEJ DMJP-UHFFF AOYSA-N | 1466 2128 91 | pubchem.ncbi. nlm.nih.gov/ compound/91 819934 |
| 7 | 1,6-anhydro-N-acetyl-β-muramate | ZFEGY UMHFZ OYTY-UHFFF AOYSA-N | 1466 2131 57 | pubchem.ncbi. nlm.nih.gov/ compound/90 658592 |
| 8 | 3-[(1-Carboxy-vinyl)oxy]benzoic acid | HGVAH YJMDV ROLE-UHFFF AOYSA-N | 1466 2118 38 | pubchem.ncbi. nlm.nih.gov/ compound/23 844017 |

TABLE 1-continued

| | | | | | |
|---|---|---|---|---|---|
| 9 | cyclic DHFL | BAUPPZJHTWBQAS-UHFFFAOYSA-N | 1466211442 | pubchem.ncbi.nlm.nih.gov/compound/44237194 | |
| 10 | 5,8-dihydroxy-2-naphthoic acid | HVZYIHBMRFYBRI-UHFFFAOYSA-N | 1466211884 | pubchem.ncbi.nlm.nih.gov/compound/14278030 | |
| 11 | futalosine | VEDWXCWBMDQNCV-UHFFFAOYSA-N | 1466212849 | pubchem.ncbi.nlm.nih.gov/compound/10364451 | |
| 12 | undecylprodigioεin | ISFCPXILUVJVOC-UHFFFAOYSA-N | 1466211950 | pubchem.ncbi.nlm.nih.gov/compound/6438379 | |
| 13 | 3,5-dioxo-6-[4,5,7-trihydroxy-3-(3-oxobutanoyl)naphthalen-2-yl]hexanoate | KQWNMCHCVXVLRS-UHFFFAOYSA-N | 1466212102 | pubchem.ncbi.nlm.nih.gov/compound/90659064 | |

| | unique_id | chebi_url | description | chebi_id |
|---|---|---|---|---|
| 1 | | | | |
| 2 | | | | |
| 3 | | | | |
| 4 | | | | |
| 5 | | | | |
| 6 | 42c6e100deb84c5ea4024515f973835b | | | |
| 7 | b617b4d0a2df4141a102193b6a1c5e73 | | | |
| 8 | 025edfdfe4b04c0790b4f9aa5323ab2d | www.ebi.ac.uk/chebi/searchId.do?chebiId=CHEBI:77107///http://www.ebi.ac.uk/chebi/searchId.do?chebiId=CHEBI:76981 | A dicarboxylic acid that is benzoic acid in which the hydrogen at position 3 is replaced by a (1-carboxyvinyl)oxy group.///A dicarboxylic acid dianion obtained by deprotonation of both carboxy groups of 3-[(1-carboxyvinyl)oxy]benzoic acid; major species at pH 7.3. | CHEBI:77107///CHEBI:76981 |
| 9 | c55df989230b4eb6b3ba7050d2a99f88 | www.ebi.ac.uk/chebi/searchId.do?chebiId=CHEBI:64270///http://www.ebi.ac.uk/chebi/searchId.do?chebiId=CHEBI:64252 | A benzoate anion that is the conjugate base of cyclic dehypoxanthinylfutalosine, arising from deprotonation of the carboxy group; major species at pH 7.3.///A oxaspiro compound obtained by formal spirocyclisation of dehypoxanthinylfutalosine. | CHEBI:64270///CHEBI:64252 |
| 10 | b012898c3d714549a5cf5d8ab64a4670 | www.ebi.ac.uk/chebi/searchId.do?chebiId=CHEBI:64254///http://www.ebi.ac.uk/chebi/searchId.do?chebiId=CHEBI:64284 | A monocarboxylic acid anion that is the conjugate base of 1,4-dihydroxy-6-naphtoic acid, arising from deprotonation of the carboxy group.///A naphthalenediol that is naphthalene-1,4-diol bering a carboxy substituent at position 6. | CHEBI:64254///CHEBI:64284 |
| 11 | dba3cb66e54e4463bbfb704d82ff99d4 | www.ebi.ac.uk/chebi/searchId.do?chebiId=CHEBI:58863///http://www.ebi.ac.uk/chebi/searchId.do?chebiId=CHEBI:51310 | A 5-oxo monocarboxylic acid anion that is the conjugate base of futalosine. | CHEBI:58863///CHEBI:51310 |

TABLE 1-continued

| | |
|---|---|
| 12 | 8bc4499 |
| | 9badb47 |
| | d6976af |
| | 3caa887 |
| | 84f1 |
| 13 | f6a8b05 |
| | b769947 |
| | caa8d5b |
| | 3ee9b24 |
| | 01ef |

MAGI reaction and reference sequence database. The MAGI reaction database was constructed by aggregating all publicly available reactions in MetaCyc and RHEA reaction databases. Identical reactions were collapsed together by calculating a "reaction InChI key," where the SMILES strings of all members of a reaction were strung together, separated by a "." and converted to a single InChI string through an RDkit (github.com/rdkit/rdkit) Mol object, and then the InChI key was calculated also using RDKit. Reactions with identical reaction InChI keys have identical chemical metabolites, indicating they are duplicates, and were collapsed into one database entry, retaining reference sequences Reference sequences for each reaction from each database were combined to create a set of curated reference sequences for each reaction in the database.

Chemical Network. In order to expand the chemical space beyond what is in the reaction database, a chemical network was constructed to relate all metabolites in the database to metabolites in reactions by biochemical similarity. In each molecule, 70 chemical features were located (Table 2). These features were defined previously as being biochemically relevant. The count of each feature was stored as a vector for each molecule. The Euclidean distance between two vectors was used to determine similarity between two molecules and construct a similarity network where every molecule is connected to every molecule by the difference in their vectors. This network was trimmed by calculating a minimum-spanning tree based on frequency of biochemical differences where more frequent differences would be preserved when possible. The chemical similarity network can be displayed as a minimum spanning tree.

TABLE 2

Description of chemical features used to calculate chemical similarity.

| Atom | Functional group | Atom type | Description | Frequency | SMARTS |
|---|---|---|---|---|---|
| C | Alkane | C1a | R—CH3 | 16473 | C[D1; C] |
| C | Alkane | C1b | R—CH2—R | 20193 | C[D2; C]C |
| C | Alkane | C1c | R—CH(—R)—R | 4964 | C[D3; C](C)C |
| C | Alkane | C1d | R—C(—R)2—R | 698 | C[D4; C](C)(C)C |
| C | Cyclic alkane | C1x | ring-CH2-ring | 14010 | [C; R][D2; C][C; R] |
| C | Cyclic alkane | C1y | ring-CH(—R)-ring | 27376 | [C; R][D3; C](C)[C; R] |
| C | Cyclic alkane | C1z | ring-C(—R)2-ring | 4463 | [C; R][D4; C](C)(C)[C; R] |
| C | Alkene | C2a | R=CH2 | 634 | C—[H2] |
| C | Alkene | C2b | R=CH—R | 3965 | [!D1; C] = [D2; C] |
| C | Alkene | C2c | R=C(—R)2 | 1914 | [!D2; !D1; C] = [C] |
| C | Cyclic alkene | C2x | ring-CH=ring | 2964 | [C; R][D2; C] = [C; R] |
| C | Cyclic alkene | C2y | ring-C(=R)-ring | 3722 | [C; R][D3; C](=C)[C; R] |
| C | Cyclic alkene | C2y | ring-C(—R)=ring | 3722 | [C; R][D3; C](C) = [C; R] |
| C | Alkyne | C3a | R#CH | 43 | C#[D1; C] |
| C | Alkyne | C3b | R#C—R | 282 | C#[D2; C] |
| C | Aldehyde | C4a | R—CH=O | 350 | O=[D2; C] |
| C | Ketone | C5a | R—C(=O)—R | 3595 | C(=O)(C)C |
| C | Cyclic ketone | C5x | ring-C(=O)-ring | 2257 | [C; R][D3; C](=O)[C; R] |
| C | Carboxylic acid | C6a | R—C(=O)—OH | 3190 | CC(=O)[D1; O] |
| C | Carboxylic ester | C7a | R—C(=O)—O—R | 1691 | CC(=O)[D2; O]C |
| C | Carboxylic ester | C7x | ring-C(=O)—O-ring | 869 | [C; R](=O)[D2; O][C; R] |
| C | Aromatic ring | C8x | ring-CH=ring | 19905 | [c; R; D2] |

TABLE 2-continued

Description of chemical features used to calculate chemical similarity.

| Atom | Functional group | Atom type | Description | Frequency | SMARTS |
|---|---|---|---|---|---|
| C | Aromatic ring | C8y | ring-C(—R)=ring | 20511 | [c; R; D3](C) |
| C | Undefined C | C0 |  | 8 | C |
| N | Amine | N1a | R—NH2 | 2440 | C[D1; N] |
| N | Amine | N1b | R—NH—R | 3003 | C[D2; N]C |
| N | Amine | N1c | R—N(—R)2 | 374 | C[D3; N](C)C |
| N | Amine | N1d | R—N(—R)3+ | 105 | C[D4; N](C)(C)C |
| N | Cyclic amine | N1x | ring-NH-ring | 806 | [R; C][R; D2; N][R; C] |
| N | Cyclic amine | N1y | ring-N(—R)-ring | 1464 | [R; C][R; D3; N](C)[R; C] |
| N | Imine | N2a | R=N—H | 230 | C=[D1; N] |
| N | Imine | N2b | R=N—R | 163 | C=[D2; N]C |
| N | Cyclic imine | N2x | ring-N=ring | 357 | [C; R] = [D2; N][C; R] |
| N | Cyclic imine | N2y | ring-N(—R)+=ring | 14 | [R; C] = [D3; N](C)[R; C] |
| N | Cyan | N3a | R#N | 119 | C#[D1; N] |
| N | Aromatic ring | N4x | ring-NH-ring | 785 | c[D2; n]c |
| N | Aromatic ring | N4y | ring-N(—R)-ring | 840 | c[D3; n](C)c |
| N | Aromatic ring | N5x | ring-N=ring | 2131 | c[D2; n]c |
| N | Aromatic ring | N5y | ring-N(—R)+=ring | 59 | c[D3; n](C)c |
| N | Undefined N | N0 |  | 194 | N |
| O | Hydroxy | O1a | R—OH | 18369 | C[D1; O] |
| O | Hydroxy | O1b | N—OH | 198 | N[D1; O] |
| O | Hydroxy | O1c | P—OH | 3111 | P[D1; O] |
| O | Hydroxy | O1d | S—OH | 332 | S[D1; O] |
| O | Ether | O2a | R—O—R | 4199 | C[D2; O]C |
| O | Ether | O2b | P—O—R | 2481 | P[D2; O]C |
| O | Ether | O2c | P—O—P | 502 | P[D2; O]P |
| O | Ether | O2x | ring-O-ring | 5853 | [R; C][R; D2; O][R; C] |
| O | Oxo | O3a | N=O | 134 | N(=O) |
| O | Oxo | O3b | P=O | 2248 | P(=O) |
| O | Oxo | O3c | S=O | 941 | S(=O) |
| O | Aldehyde | O4a | R—CH=O | 350 | O=[D2; C] |
| O | Ketone | O5a | R—C(=O)—R | 3595 | C(=O)(C)C |
| O | Ketone | O5x | ring-C(=O)-ring | 2862 | [R; C][R; D3; C](—O)[R; C] |
| O | Carboxylic acid | O6a | R—C(=O)—OH | 6384 | CC(=O)[D1; O] |
| O | Ester | O7a | R—C(=O)—O—R | 3382 | CC(=O)[D2; O]C |
| O | Ester | O7x | ring-C(=O)—O-ring | 1738 | [R; C][R; C](=O)[R; O] |
| O | Ester | O7x | ring-C(=O)—O-ring | 1738 | c[R; c](=O)o |
| O | Undefined O | O0 |  | 127 | O |
| S | Thiol | S1a | R—SH | 100 | C[D1; S] |
| S | Thioether | S2a | R—S—R | 420 | C[D2; S]C |
| S | Thioether | S2x | ring-S-ring | 261 | [R; C; D2][R; D2; S][R; C; D2] |
| S | Disulfide | S3a | R—S—S—R | 45 | C[D2; S][D2; S]C |
| S | Disulfide | S3x | ring-S—S-ring | 48 | [R; C; D2][R; D2; S][R; D2; S][R; C; D2] |
| S | Sulfate | S4a | R—SO3 | 267 | S(O)(O)(O) |
| S | Undefined S | S0 |  | 223 | S |
| P | Attached to other elements | P1a | P—R | 112 | CP |
| P | Attached to oxygen | P1b | P—O | 2158 | PO |
| Other | Halogens | X | F, Cl, Br, I | 1419 | [F, Cl, Br, I] |
| Other | Others | Z |  | 261 | * |

Gene Annotations of *Streptomyces coelicolor*. KEGG annotations were obtained by submitting the *S. coelicolor* protein FASTA obtained from IMG to the KEGG Automatic Annotation Server version 2.1 and downloading the gene-KO results table. KO numbers were associated with reactions by assessing if there was a link to one or more KEGG reaction entries directly from the webpage of that KO. For BioCyc annotations and reactions, the BioCyc *S. coelicolor* database downloaded. For the reactions in Table 3, KEGG and BioCyc reactions were manually inspected and compared to MAGI reactions.

Data Availability

All source code available at github.com/biorack/magi, and the *S. coelicolor* mass spectrometry data (.mzML files) and MIDAS results (metabolite_0ae82b08.csv) can be found here: magi.nersc.gov/jobs/?id=0ae82b08-b2a3-40d8-bb9a-e64b567eacd2.

Results and Discussion

Improved metabolite identification for metabolomics. To demonstrate how MAGI uses genomic information to filter and score possible metabolite identities from a metabolomics experiment, sequencing and metabolomics data were

TABLE 3

Comparison between MAGI, KEGG, and BioCyC annotations for *S. coelicolor* genes discussed in this study.

| Gene | MAGI annotation (reaction) | MAGI score | Observed Metabolite Evidence | KEGG annotation (name) | KEGG Reaction Agreement with MAGI | BioCyc annotation (name) | BioCyc Reaction Agreement with MAGI | Note |
|---|---|---|---|---|---|---|---|---|
| SCO4326 | RXN-10622 | 5.68 | Dihydroxy-naphthoate | 1,4-dihydroxy-6-naphthoate synthase | Agree | ORF | None | Menaquinone biosynthesis pathway |
| SCO4327 | RHEA: 25907 | 5.16 | Futalosine | None | None | ORF | None | |
| SCO4494 | RXN-15264 | 5.57 | Carboxy-vinyloxy-benzoic acid | Aminodeoxy-futalosine synthase | Agree | ORF | None | |
| SCO4506 | RXN-12345 | 5.57 | Carboxy-vinyloxy-benzoic acid | chorismate dehydratase | Agree | ORF | None | |
| SCO4550 | RXN-10620 | 5.03 | Cyclic-DHFL | cyclic dehypoxanthinyl futalosine synthase | Agree | ORF | None | |
| SCO5074 | RXN1A0-6312 | 5.37 | Bicyclic intermediate F & (S)-Hemiketal | None | None | ActVI ORF3 | Agree | Actinorhodin biosynthesis pathway |
| SCO5075 | RXN1A0-6316 | 1.22 | Dihydro-kalafungin | None | None | ActVI-ORF4 | Agree | |
| SCO5080 | RXN-18115 | 4.87 | DHK-red | 3-hydroxy-9,10-secoandrosta-1,3,5(10)-triene-9,17-dione monooxygenase [EC:1.14.14.12] | Disagree: R09819 | ActVA-ORF5 | Agree | |
| SCO5081 | RXN1A0-6318 | 4.63 | Dihydro-kalafungin | None | None | ActVA-ORF6 | Agree | |
| SCO5091 | RXN1A0-6307 | 5.95 | Bicyclic intermediate E | None | None | ActIV | Agree | |
| SCO5315 | RXN-15413 | 4.58 | WhiE_20C_substrate | None | None | Polyketide aromatase | None | Known WhiE protein function |
| SCO5896 | RXN-15787* | 1.32 | Undecyl-prodigiosin | pyruvate, water dikinase | Disagree: R00199 | RedH | Agree* | Known undecyl-prodigiosin synthase |
| SCO6300 | RXN0-5226 | 3.22 | Anhydro-NAM | beta-N-acetyl-hexosaminidase | Disagree: R00022, R05963, R07809, R07810, R10831 | hydrolase | None | Additional Evidence for vague or nonexistent gene annotations |
| SCO7595 | RHEA: 24952 | 5.23 | Anhydro-NAM | anhydro-N-acetylmuramic acid kinase | None | ORF | None | |

*Due to chemical network search, this reaction was listed as the prodigiosin synthase reaction but the metabolite connected to it was undecylprodigiosin, requiring manual interpretation to determine the actual reaction connected to the gene was undecylprodigiosin synthase.

obtained for *S. coelicolor*. After processing the raw LCMS data to find chromatograms and peaks, 878 features with a unique m/z and retention time were found in the dataset. After neutralizing the m/z values, accurate mass searching, and conducting MS/MS fragmentation pattern analysis, 6,604 unique metabolite structures were tentatively associated with these features (Table 4), that is, for each feature there were almost 8 candidate structures on average. All candidate structures for each feature had at least one fragmentation spectrum that matched to its theoretical fragmentation pattern, highlighting the difficulty of unambiguous metabolite identification. 2,786 of these structures were then linked to a total of 10,265 reactions either directly or via the chemical similarity network, and the reactions were associated with 3,181 (out of 8,210) *S. coelicolor* genes by homology. Finally, a MAGI score was calculated for each metabolite-reaction-gene association (Table 5).

TABLE 4

MIDAS results for a subset of the *S. coelicolor* metabolomics dataset.

| feature | Suggested metabolite (InChIKey Format) | Metabolite score |
|---|---|---|
| 125.0231@4.58 | DLEGDLSLRSOURQ-UHFFFAOYSA-N | 0.687245562 |
| 125.0232@4.46 | NSYSSMYQPLSPOD-UHFFFAOYSA-N | 0.544771215 |
| 125.0232@4.46 | LCOGJKFAVXDKBI-PHDIDXHHSA-N | 0.540585314 |
| 125.0232@4.46 | RSZZMVPSHLKFQY-UHFFFAOYSA-N | 0.531177389 |
| 125.0232@4.46 | GGNQRNBDZQJCCN-UHFFFAOYSA-N | 0.53936211 |
| 125.0232@4.46 | OVOCLWJUABOAPL-UHFFFAOYSA-N | 0.533727084 |
| 125.0232@4.46 | NPMQEIOINVDLMV-UHFFFAOYSA-N | 0.538524313 |
| 125.0232@4.46 | RQZSMDBBVOOYQY-UHFFFAOYSA-N | 0.533721402 |
| 125.0232@4.46 | HDJLSECJEQSPKW-UHFFFAOYSA-N | 0.530957026 |

TABLE 4-continued

MIDAS results for a subset of the *S. coelicolor* metabolomics dataset.

| feature | Suggested metabolite (InChIKey Format) | Metabolite score |
|---|---|---|
| 125.0232@4.46 | QCDYQQDYXPDABM-UHFFFAOYSA-N | 0.541235204 |
| 125.0232@4.46 | MFGALGYVFGDXIX-UHFFFAOYSA-N | 0.541726672 |
| 125.0232@4.46 | NOEGNKMFWQHSLB-UHFFFAOYSA-N | 0.537605083 |
| 125.0232@4.46 | XPCTZQVDEJYUGT-UHFFFAOYSA-N | 0.546101253 |
| 125.0232@4.46 | QNXPRMJHYUHYKW-UHFFFAOYSA-N | 0.537334358 |
| 125.0232@4.46 | HPIGCVXMBGOWTF-UHFFFAOYSA-N | 0.539591126 |
| 125.0232@4.46 | WQGWDDDVZFFDIG-UHFFFAOYSA-N | 0.537489017 |
| 125.0232@4.46 | IZYQYTLECIJWMX-UHFFFAOYSA-N | 0.530077338 |
| 125.0232@4.46 | RFTMILUWMDIPHH-NSCUHMNNSA-N | 0.543395878 |
| 125.0232@4.46 | DLEGDLSLRSOURQ-UHFFFAOYSA-N | 0.687245562 |
| 125.0232@4.46 | HITOXZPZGPXYHY-UJURSFKZSA-N | 0.540911518 |
| 125.0232@4.46 | ZNUNRMPPGAAKKR-UHFFFAOYSA-N | 0.55005639 |
| 125.0233@1.04 | NPMQEIOINVDLMV-UHFFFAOYSA-N | 0.661304259 |
| 125.0233@1.04 | RSZZMVPSHLKFQY-UHFFFAOYSA-N | 0.636933419 |
| 125.0233@1.04 | NOEGNKMFWQHSLB-UHFFFAOYSA-N | 0.668557553 |
| 125.0233@1.04 | RFTMILUWMDIPHH-NSCUHMNNSA-N | 0.681420118 |
| 125.0233@1.04 | OVOCLWJUABOAPL-UHFFFAOYSA-N | 0.634099619 |
| 125.0233@1.04 | LCOGJKFAVXDKBI-PHDIDXHHSA-N | 0.669685883 |
| 125.0233@1.04 | MFGALGYVFGDXIX-UHFFFAOYSA-N | 0.647897633 |
| 125.0233@1.04 | QCDYQQDYXPDABM-UHFFFAOYSA-N | 0.673986651 |
| 125.0233@1.04 | WQGWDDDVZFFDIG-UHFFFAOYSA-N | 0.66004202 |
| 125.0233@1.04 | HPIGCVXMBGOWTF-UHFFFAOYSA-N | 0.655094582 |
| 125.0233@1.04 | ZNUNRMPPGAAKKR-UHFFFAOYSA-N | 0.695300918 |
| 125.0233@1.04 | HDJLSECJEQSPKW-UHFFFAOYSA-N | 0.635233749 |
| 125.0233@1.04 | RQZSMDBBVOOYQY-UHFFFAOYSA-N | 0.632392924 |
| 125.0233@1.04 | XPCTZQVDEJYUGT-UHFFFAOYSA-N | 0.684678031 |
| 125.0233@1.04 | HITOXZPZGPXYHY-UJURSFKZSA-N | 0.675265549 |
| 125.0233@1.04 | IZYQYTLECIJWMX-UHFFFAOYSA-N | 0.612111548 |
| 125.0233@1.04 | QNXPRMJHYUHYKW-UHFFFAOYSA-N | 0.657980112 |

TABLE 5

Reactions associated with some *S. coelicoloar* genes by BioCyc, KEGG, and MAGI.

| IMG Gene ID | Locus_Tag | n_reactions_BioCyc | n_reactions_KEGG | n_reactions_MAGI | MAGI Connection to Metabolite | Top MAGI score |
|---|---|---|---|---|---|---|
| 637264255 | SCO0001 | 0 | 0 | 0 | No | |
| 637264256 | SCO0002 | 0 | 0 | 1 | Yes | 0.03700293 |
| 637264257 | SCO0003 | 0 | 0 | 0 | No | |
| 637264258 | SCO0004 | 0 | 0 | 1 | No | |
| 637264259 | SCO0005 | 0 | 0 | 0 | No | |
| 637264260 | SCO0006 | 0 | 0 | 1 | No | |
| 637264261 | SCO0007 | 0 | 0 | 0 | No | |
| 637264262 | SCO0008 | 0 | 0 | 0 | No | |
| 637264263 | SCO0009 | 0 | 0 | 0 | No | |
| 637264264 | SCO0010 | 0 | 0 | 0 | No | |
| 637264265 | SCO0011 | 0 | 0 | 0 | No | |
| 637264266 | SCO0012 | 0 | 0 | 1 | Yes | 1.303646507 |
| 637264267 | SCO0013 | 0 | 0 | 0 | No | |
| 637264268 | SCO0014 | 0 | 0 | 1 | No | |
| 637264269 | SCO0015 | 1 | 0 | 0 | No | |
| 637264270 | SCO0016 | 0 | 0 | 2 | No | |
| 637264271 | SCO0017 | 0 | 0 | 0 | No | |
| 637264272 | SCO0018 | 0 | 0 | 0 | No | |
| 637264273 | SCO0019 | 0 | 0 | 0 | No | |
| 637264274 | SCO0020 | 0 | 0 | 0 | No | |
| 637264275 | SCO0021 | 0 | 0 | 0 | No | |
| 637264276 | SCO0022 | 0 | 0 | 0 | No | |
| 637264277 | SCO0025 | 0 | 0 | 0 | No | |
| 637264278 | SCO0026 | 0 | 0 | 0 | No | |
| 637264279 | SCO0027 | 0 | 0 | 0 | No | |
| 637264280 | SCO0028 | 0 | 0 | 3 | No | |
| 637264281 | SCO0029 | 0 | 0 | 0 | No | |
| 637264282 | SCO0030 | 0 | 0 | 0 | No | |
| 637264283 | SCO0031 | 0 | 0 | 1 | No | |
| 637264284 | SCO0032 | 0 | 0 | 0 | No | |
| 637264285 | SCO0033 | 1 | 0 | 1 | Yes | 0.419554229 |
| 637264286 | SCO0034 | 0 | 0 | 0 | No | |
| 637264287 | SCO0035 | 0 | 0 | 1 | No | |

TABLE 5-continued

Reactions associated with some S. coelicoloar genes by BioCyc, KEGG, and MAGI.

| IMG Gene ID | Locus_Tag | n_reactions_BioCyc | n_reactions_KEGG | n_reactions_MAGI | MAGI Connection to Metabolite | Top MAGI score |
|---|---|---|---|---|---|---|
| 637264288 | SCO0036 | 0 | 0 | 1 | No | |
| 637264289 | SCO0037 | 0 | 0 | 0 | No | |
| 637264290 | SCO0038 | 0 | 0 | 0 | No | |
| 637264291 | SCO0039 | 0 | 0 | 2 | No | |

An example that illustrates MAGI's utility in metabolite identification was the identification of 1,4-dihydroxy-6-naphthoic acid. Here, a feature with an m/z of 203.0345 was observed. This feature was associated with the chemical formula $C_{11}H_8O_4$, which could be derived from 16 unique chemical structures in the metabolite database (Table 6). Mass fragmentation spectra were collected for this feature and analyzed using MIDAS, a tool that scores the observed fragmentation spectrum against its database of in-silico fragmentation trees for the 16 potential structures. Based only on the MIDAS metabolite score, the top scoring structure was 5,6-dihydroxy-2-methylnaphthalene-1,4-dione. However, after calculating the MAGI scores, a different metabolite received the highest score. Of the 16 potential metabolites, only 1,4-dihydroxy-6-naphthoic acid was in a reaction that had a perfect match to genes in S. coelicolor (an E-value of 0.0 to SCO4326; Table 3). This metabolite is a known intermediate in an alternative menaquinone biosynthesis pathway discovered in S. coelicolor, making it much more likely to be a metabolite detected from the metabolome of S. coelicolor as opposed to the metabolite found just by looking at mass fragmentation alone.

TABLE 6

Subset of MIDAS metabolite suggestions for the feature with m/z 203.0345

| Feature | Suggested metabolite (InChIKey Format) | metabolite score |
|---|---|---|
| 203.0345@3.07 | HWWWTOHAFWXPCB-UHFFFAOYSA-N | 1.030240775 |
| 203.0345@3.07 | YKPXIWHBRBFRQM-UHFFFAOYSA-N | 1.030112081 |
| 203.0345@3.07 | CQDXJBJBEQPBEM-UHFFFAOYSA-N | 0.941043327 |
| 203.0345@3.07 | STTBYRIXKIKKPR-UHFFFAOYSA-N | 0.941043327 |
| 203.0345@3.07 | OUKZWTCVYRLZAW-UHFFFAOYSA-N | 0.832492644 |
| 203.0345@3.07 | OHLFONANHBAJJF-UHFFFAOYSA-N | 0.653333666 |
| 203.0345@3.07 | CQDYYFBBSBVPHU-UHFFFAOYSA-N | 0.653333666 |
| 203.0345@3.07 | GATGZQSBJAZYRT-UHFFFAOYSA-N | 0.653333666 |
| 203.0345@3.07 | ZKEVGLUAKGKGMO-UHFFFAOYSA-N | 0.649582665 |
| 203.0345@3.07 | VOJUXHHACRXLTD-UHFFFAOYSA-N | 0.648596239 |
| 203.0345@3.07 | HVZYIHBMRFYBRI-UHFFFAOYSA-N | 0.648596239 |
| 203.0345@3.07 | XYOABSOIKCDDDO-UHFFFAOYSA-N | 0.564805285 |
| 203.0345@3.07 | BFQZCXJRQTUNQG-UHFFFAOYSA-N | 0.473961735 |
| 203.0345@3.07 | HOFSOQDUZIZMBA-UHFFFAOYSA-N | 0.473961646 |
| 203.0345@3.07 | MGZOXZPZHVOXQB-UHFFFAOYSA-N | 0.373114888 |
| 203.0345@3.07 | WWHMQTDCCWMKQY-YTWAJWBKSA-N | 0.188534242 |

Metabolomics-driven gene annotations. MAGI keeps the biochemical potential of an organism unconstrained by considering a plurality of probable gene product functions. One effect of this was that more reactions were associated with genes than other services (FIG. 6A). Because reactions are the pivotal link between metabolites and genes, this allowed integration of a larger fraction of a metabolomics dataset with genes. Furthermore, MAGI associated many genes that have not been annotated using traditional approaches with at least one reaction (FIG. 6B). Out of a total of 8,210 predicted coding sequences in S. coelicolor, KEGG and BioCyc had one or more reactions associated with 1,106 and 1,294 genes, respectively. On the oilier hand, MAGI associated 5,209 genes with one or more reactions, out of which 3,719 genes had no reaction associated with them in either KEGG or BioCyc (FIG. 6B). Of these 3,719 genes, 1,883 were linked to at least one metabolite in the metabolomics data (Table 5). Certainly, not all MAGI gene-reaction associations may be correct, though this does provide many testable hypotheses that give footholds to discover new biochemistry; as can be seen in FIG. 6C, many of these new gene-reaction associations have high scores, indicating a likely connection.

Validation of gene-metabolite integration in pathways. One of the most well-known biosynthetic pathways in S. coelicolor is the pathway to synthesize the pigmented antibiotic actinorhodin. The MAGI results involving the metabolites and genes of actinorhodin biosynthesis were examined as a proof-of-principle that MAGI successfully integrated metabolites and genes, and that these results can be mapped onto a reaction network. Actinorhodin and all of its detected intermediates were correctly identified and accurately mapped to the correct genes (FIG. 7A), despite some intermediates having several plausible metabolite identities (Table 7). Notably, KEGG did not annotate the majority of actinorhodin biosynthesis genes, and the one gene that it did annotate was incorrect (Table 3).

TABLE 7

MAGI results of some genes in the actinorhodin biosynthesis pathway.

| | label | original_compound (InChIKey Format) | MAGI_score | level | Neighbor (InChIKey Format) |
|---|---|---|---|---|---|
| 1 | 301.0724@5.07 | PBONQNRANFYEQU-UHFFFAOYSA-N | 5.798101731 | 0 | |
| 2 | 301.0724@5.07 | PBONQNRANFYEQU-UHFFFAOYSA-N | 5.798101731 | 0 | |

TABLE 7-continued

| | | | | |
|---|---|---|---|---|
| 3 | 301.0724@5.07 | PBONQNRANFYEQU-UHFFFAOYSA-N | 4.875602961 | 0 |
| 4 | 301.0724@5.07 | ZCJHPTKRISJQTN-SFYZADRCSA-N | 4.497594052 | 0 |
| 5 | 301.0724@5.07 | ZCJHPTKRISJQTN-JGVFFNPUSA-N | 4.497594052 | 0 |
| 6 | 301.0724@5.07 | FTODBIPDTXRIGS-ZDUSSCGKSA-N | 2.475377866 | 0 |
| 7 | 301.0724@5.07 | FTODBIPDTXRIGS-ZDUSSCGKSA-N | 2.475377866 | 0 |
| 8 | 301.0724@5.07 | FTODBIPDTXRIGS-ZDUSSCGKSA-N | 2.475377866 | 0 |
| 9 | 301.0724@5.07 | FTODBIPDTXRIGS-CYBMUJFWSA-N | 2.475377866 | 0 |
| 10 | 301.0724@5.07 | FTODBIPDTXRIGS-CYBMUJFWSA-N | 2.475377866 | 0 |
| 11 | 301.0724@5.07 | FTODBIPDTXRIGS-CYBMUJFWSA-N | 2.475377866 | 0 |
| 12 | 301.0724@5.07 | FTODBIPDTXRIGS-UHFFFAOYSA-N | 2.475377866 | 0 |
| 13 | 301.0724@5.07 | FTODBIPDTXRIGS-UHFFFAOYSA-N | 2.475377866 | 0 |
| 14 | 301.0724@5.07 | FTODBIPDTXRIGS-UHFFFAOYSA-N | 2.475377866 | 0 |
| 15 | 301.0724@5.07 | AIONOLUJZLIMTK-AWEZNQCLSA-N | 2.475323703 | 0 |
| 16 | 301.0724@5.07 | AIONOLUJZLIMTK-AWEZNQCLSA-N | 2.475323703 | 0 |
| 17 | 301.0724@5.07 | AIONOLUJZLIMTK-AWEZNQCLSA-N | 2.475323703 | 0 |
| 18 | 301.0724@5.07 | AIONOLUJZLIMTK-UHFFFAOYSA-N | 2.475323703 | 0 |
| 19 | 301.0724@5.07 | AIONOLUJZLIMTK-UHFFFAOYSA-N | 2.475323703 | 0 |
| 20 | 301.0724@5.07 | AIONOLUJZLIMTK-UHFFFAOYSA-N | 2.475323703 | 0 |
| 21 | 301.0724@5.07 | NTPLIZCSFKSXCB-UHFFFAOYSA-N | 0.77556481 | 0 |
| 22 | 301.0724@5.07 | NTPLIZCSFKSXCB-UHFFFAOYSA-N | 0.77556481 | 0 |
| 23 | 301.0724@5.07 | NTPLIZCSFKSXCB-UHFFFAOYSA-N | 0.77556481 | 0 |
| 24 | 301.0724@5.07 | NTPLIZCSFKSXCB-UHFFFAOYSA-N | 0.77556481 | 0 |
| 25 | 301.0724@5.07 | NTPLIZCSFKSXCB-UHFFFAOYSA-N | 0.77556481 | 0 |
| 26 | 301.0724@5.07 | NTPLIZCSFKSXCB-UHFFFAOYSA-N | 0.77556481 | 0 |
| 27 | 301.0724@5.07 | NTPLIZCSFKSXCB-UHFFFAOYSA-N | 0.77556481 | 0 |
| 28 | 301.0724@5.07 | IIQJLBKXWGKSKE-CZUORRHYSA-N | 0.663379645 | 0 |
| 29 | 301.0724@5.07 | IIQJLBKXWGKSKE-CZUORRHYSA-N | 0.663379645 | 0 |
| 30 | 301.0724@5.07 | IIQJLBKXWGKSKE-CZUORRHYSA-N | 0.663379645 | 0 |
| 31 | 301.0724@5.07 | FDUZTVVNKDZMKG-INIZCTEOSA-N | 0.606877608 | 0 |
| 32 | 301.0724@5.07 | VGLBFRZJJZBAST-ZBEGNZNMSA-N | 0.570126538 | 0 |
| 33 | 301.0724@5.07 | VGLBFRZJJZBAST-ZBEGNZNMSA-N | 0.558530697 | 0 |
| 34 | 301.0724@5.07 | ZCJHPTKRISJQTN-SFYZADRCSA-N | 0.476660993 | 1 | BGCANOPAKSHGIV-KCJUWKMLSA-N |
| 35 | 301.0724@5.07 | ZCJHPTKRISJQTN-SFYZADRCSA-N | 0.476660993 | 1 | BGCANOPAKSHGIV-KCJUWKMLSA-N |
| 36 | 301.0724@5.07 | ZCJHPTKRISJQTN-SFYZADRCSA-N | 0.476660993 | 1 | BGCANOPAKSHGIV-KCJUWKMLSA-N |
| 37 | 301.0724@5.07 | ZCJHPTKRISJQTN-JGVFFNPUSA-N | 0.476660993 | 1 | BGCANOPAKSHGIV-KCJUWKMLSA-N |
| 38 | 301.0724@5.07 | ZCJHPTKRISJQTN-JGVFFNPUSA-N | 0.476660993 | 1 | BGCANOPAKSHGIV-KCJUWKMLSA-N |

| | compound_score | homology_score | reciprocal_score | query acc. | database_id_r2g | database_id_g2r |
|---|---|---|---|---|---|---|
| 1 | 0.70284131 | 400 | 2 | 637269366 | RXN1A0-6307 | RXN1A0-6307 |
| 2 | 0.70284131 | 400 | 2 | 637269347 | RXN1A0-6310 | RXN1A0-6310 |
| 3 | 0.70284131 | 400 | 1 | 637269366 | RXN1A0-6307 | RXN-15199 |
| 4 | 0.642070041 | 158.5304003 | 2 | 637269356 | RXN1A0-6318 | RXN1A0-6318 |
| 5 | 0.642070041 | 158.5304003 | 2 | 637269356 | RXN1A0-6318 | RXN1A0-6318 |
| 6 | 0.488315356 | 38.2533588 | 1 | 637266572 | RXN-7753 | RHEA:21821 |
| 7 | 0.488315356 | 38.2533588 | 1 | 637266572 | RXN-7753 | RHEA:26340 |
| 8 | 0.488315356 | 38.2533588 | 1 | 637266572 | RXN-7753 | RHEA:16927 |
| 9 | 0.488315356 | 38.2533588 | 1 | 637266572 | RXN-7753 | RHEA:26340 |
| 10 | 0.488315356 | 38.2533588 | 1 | 637266572 | RXN-7753 | RHEA:16927 |
| 11 | 0.488315356 | 38.2533588 | 1 | 637266572 | RXN-7753 | RHEA:21821 |
| 12 | 0.488315356 | 38.2533588 | 1 | 637266572 | RXN-7753 | RHEA:26340 |
| 13 | 0.488315356 | 38.2533588 | 1 | 637266572 | RXN-7753 | RHEA:16927 |
| 14 | 0.488315356 | 38.2533588 | 1 | 637266572 | RXN-7753 | RHEA:21821 |
| 15 | 0.488272619 | 38.2533588 | 1 | 637266572 | RXN-7754 | RHEA:16927 |
| 16 | 0.488272619 | 38.2533588 | 1 | 637266572 | RXN-7754 | RHEA:21821 |
| 17 | 0.488272619 | 38.2533588 | 1 | 637266572 | RXN-7754 | RHEA:26340 |
| 18 | 0.488272619 | 38.2533588 | 1 | 637266572 | RXN-7754 | RHEA:21821 |
| 19 | 0.488272619 | 38.2533588 | 1 | 637266572 | RXN-7754 | RHEA:26340 |
| 20 | 0.488272619 | 38.2533588 | 1 | 637266572 | RXN-7754 | RHEA:16927 |
| 21 | 0.435122135 | 41.36805931 | 0.01 | 637269500 | RXN-14754 | RHEA:32439 |
| 22 | 0.435122135 | 41.36805931 | 0.01 | 637269500 | RXN-14754 | RHEA:25981 |
| 23 | 0.435122135 | 41.36805931 | 0.01 | 637269500 | RXN-14754 | RHEA:16917 |
| 24 | 0.435122135 | 41.36805931 | 0.01 | 637269500 | RXN-14754 | RHEA:25988 |
| 25 | 0.435122135 | 41.36805931 | 0.01 | 637269500 | RXN-14754 | RHEA:25976 |

TABLE 7-continued

| | | | | | |
|---|---|---|---|---|---|
| 26 | 0.435122135 | 41.36805931 | 0.01 | 637269500 RXN-14754 | RHEA:25984 |
| 27 | 0.435122135 | 41.36805931 | 0.01 | 637269500 RXN-14754 | RHEA:27426 |
| 28 | 0.416601222 | 23.12767471 | 0.01 | 637271402 RXN-5502 | RXN-15638 |
| 29 | 0.416601222 | 23.12767471 | 0.01 | 637271402 RXN-5502 | RXN-17615 |
| 30 | 0.416601222 | 23.12767471 | 0.01 | 637271402 RXN-5502 | RXN-13126 |
| 31 | 0.424185531 | 15.90935404 | 0.01 | 637271721 RXN-16545 | RXN-17982 |
| 32 | 0.407332865 | 12.90445059 | 0.01 | 637269354 RXN-3768 | RHEA:10623 |
| 33 | 0.407332865 | 11.8861903 | 0.01 | 637271641 RXN-3768 | RHEA:23918 |
| 34 | 0.642070041 | 400 | 2 | 637269350 RXN1A0-6316 | RXN1A0-6316 |
| 35 | 0.642070041 | 400 | 2 | 637269355 RXN-18114 | RXN-18114 |
| 36 | 0.642070041 | 400 | 2 | 637269348 RXN1A0-6316 | RXN1A0-6316 |
| 37 | 0.642070041 | 400 | 2 | 637269350 RXN1A0-6316 | RXN1A0-6316 |
| 38 | 0.642070041 | 400 | 2 | 637269348 RXN1A0-6316 | RXN1A0-6316 |

In another example, the menaquinone biosynthesis pathway, which is essential for respiration in bacteria and thus should be included in every metabolic reconstruction for organisms that produce menaquinone, was examined. An alternative menaquinone biosynthesis pathway was recently discovered and validated in *S. coelicolor*, serving as another proof-of-principle exercise for assessing the MAGI platform. MAGI linked 4 of 7 intermediate metabolites of the pathway to the appropriate genes (FIG. 7B, Table 8). Interestingly, while KEGG accurately assigned reactions to all but one of the genes in this biosynthetic pathway, BioCyC had vague textual annotations and no reactions (Table 3). Therefore, a metabolomics tool that relies on BioCyc model for *S. coelicolor* would be unable to integrate any of these metabolites with genes for the purpose of either improved metabolite identifications or gene annotations.

TABLE 8

MAGI results for genes in the menaquinone biosynthesis pathway.

| | label | original_compound (InChIKey Format) | MAGI_score | level | neighbor |
|---|---|---|---|---|---|
| 1 | 203.0345@3.07 | HVZYIHBMRFYBRI-UHFFFAOYSA-N | 5.682835929 | 0 | |
| 2 | 203.0345@3.07 | WWHMQTDCCWMKQY-YTWAJWBKSA-N | 0.117178399 | 0 | |
| 3 | 203.0345@3.07 | HOFSOQDUZIZMBA-UHFFFAOYSA-N | 0.14754884 | 0 | |
| 4 | 203.0345@3.07 | BFQZCXJRQTUNQG-UHFFFAOYSA-N | 0.147548847 | 0 | |
| 5 | 203.0345@3.07 | XYOABSOIKCDDDO-UHFFFAOYSA-N | 0.15416106 | 0 | |
| 6 | 203.0345@3.07 | ZKEVGLUAKGKGMO-UHFFFAOYSA-N | 0.159646208 | 0 | |
| 7 | 203.0345@3.07 | GATGZQSBJAZYRT-UHFFFAOYSA-N | 0.159876179 | 0 | |
| 8 | 203.0345@3.07 | CQDYYFBBSBVPHU-UHFFFAOYSA-N | 0.159876179 | 0 | |
| 9 | 203.0345@3.07 | OHLFONANHBAJJF-UHFFFAOYSA-N | 0.159876179 | 0 | |
| 10 | 203.0345@3.07 | OUKZWTCVYRLZAW-UHFFFAOYSA-N | 0.169861557 | 0 | |
| 11 | 203.0345@3.07 | STTBYRIXKIKKPR-UHFFFAOYSA-N | 0.17514688 | 0 | |
| 12 | 203.0345@3.07 | YKPXIWHBRBFRQM-UHFFFAOYSA-N | 0.179151777 | 0 | |
| 13 | 203.0345@3.07 | HWWWTOHAFWXPCB-UHFFFAOYSA-N | 0.179157372 | 0 | |
| 14 | 203.0345@3.07 | MGZOXZPZHVOXQB-UHFFFAOYSA-N | 0.770257012 | 1 | HXVZGASCDAGAPS-UHFFFAOYSA-N |
| 15 | 203.0345@3.07 | VOJUXHHACRXLTD-UHFFFAOYSA-N | 3.241196745 | 0 | |
| 16 | 203.0345@3.07 | CQDXJBJBEQPBEM-UHFFFAOYSA-N | 0.17514688 | 0 | |
| 17 | 207.0297@3.11 | FBJMEOFSLTXPKH-UHFFFAOYSA-N | 0.123165015 | 0 | |
| 18 | 207.0297@3.11 | GUKBSZIPEVVOGO-UHFFFAOYSA-N | 0.116316909 | 0 | |
| 19 | 207.0297@3.11 | CDIRPHSIKVTLRY-UHFFFAOYSA -N | 0.115944228 | 0 | |
| 20 | 207.0297@3.11 | JMJBXDWFZVLFDK-UHFFFAOYSA-N | 0.114217639 | 0 | |
| 21 | 207.0297@3.11 | HAVWRBANWNTOJX-UHFFFAOYSA-N | 0.113337808 | 0 | |
| 22 | 207.0297@3.11 | BKFBBKNNGTZBPF-UHFFFAOYSA-N | 0.1106114 | 0 | |
| 23 | 207.0297@3.11 | RDPKGUWIMLIBCM-UHFFFAOYSA-N | 0.118689267 | 0 | |
| 24 | 207.0297@3.11 | JUVHLXCMFDJFQF-UHFFFAOYSA-N | 0.108226657 | 0 | |
| 25 | 207.0297@3.11 | KLBSSFLIZVTENH-UHFFFAOYSA-N | 0.10717616 | 0 | |
| 26 | 207.0297@3.11 | HGVAHYJMDVROLE-UHFFFAOYSA-N | 4.658895627 | 0 | |
| 27 | 207.0297@4.70 | FBJMEOFSLTXPKH-UHFFFAOYSA-N | 0.141063988 | 0 | |
| 28 | 207.0297@4.70 | HGVAHYJMDVROLE-UHFFFAOYSA-N | 5.568110298 | 0 | |
| 29 | 207.0297@4.70 | JUVHLXCMFDJFQF-UHFFFAOYSAN | 0.117264674 | 0 | |
| 30 | 207.0297@4.70 | KLBSSFLIZVTENH-UHFFFAOYSA-N | 0.122094973 | 0 | |
| 31 | 207.0297@4.70 | BKFBBKNNGTZBPF-UHFFFAOYSA-N | 0.123405519 | 0 | |
| 32 | 207.0297@4.70 | GUKBSZIPEVVOGO-UHFFFAOYSA-N | 0.127014464 | 0 | |
| 33 | 207.0297@4.70 | CDIRPHSIKVTLRY-UHFFFAOYSA-N | 0.132187741 | 0 | |
| 34 | 207.0297@4.70 | HAVWRBANWNTOJX-UHFFFAOYSA-N | 0.130116992 | 0 | |
| 35 | 207.0297@4.70 | JMJBXDWFZVLFDK-UHFFFAOYSA-N | 0.129845552 | 0 | |
| 36 | 207.0297@4.70 | RDPKGUWIMLIBCM-UHFFFAOYSA-N | 0.137147466 | 0 | |
| 37 | 293.0675@3.05 | MQFZWJTXPQRJEY-UHFFFAOYSA-N | 0.117509017 | 0 | |
| 38 | 293.0675@3.05 | UHZJMMJGXFWMBG-UHFFFAOYSA-N | 0.130017089 | 0 | |
| 39 | 293.0675@3.05 | IWUGKOQICVHWPE-UHFFFAOYSA-N | 0.113157729 | 0 | |
| 40 | 293.0675@3.05 | SDORNFBUOMQVCA-RXMQYKEDSA-N | 0.114158195 | 0 | |
| 41 | 293.0675@3.05 | BAUPPZJHTWBQAS-ZZWXXDIBSA-N | 5.030019985 | 0 | |
| 42 | 293.0675@3.05 | JQSMULVYCAVOOF-STBHKTOQSA-N | 0.118520216 | 0 | |
| 43 | 293.0675@3.05 | VNPXVJGFPXCSBE-SHLVKXSWSA-N | 0.118347944 | 0 | |
| 44 | 293.0675@3.05 | CBFUBOALPHKYAS-UHFFFAOYSA-N | 0.117788487 | 0 | |

TABLE 8-continued

| | | | | | |
|---|---|---|---|---|---|
| 45 | 293.0675@3.05 | KYFKUQZHXQMABC-UHFFFAOYSA-N | 0.117426181 | 0 | |
| 46 | 293.0675@3.05 | SNBAWTHXVVSPPU-WXHSDQCUSA-N | 0.144295848 | 0 | |
| 47 | 413.1115@4.16 | VEDWXCWBMDQNCV-SCFUHWHPSA-N | 5.657174308 | 0 | |
| 48 | 413.1115@4.16 | KPVLDYMZFUPBJG-VHXBZSDJSA-N | 0.134834289 | 0 | |
| 49 | 413.1115@4.16 | IBIPGYWNOBGEMH-DILZHRMZSA-N | 0.133144546 | 0 | |
| 50 | 413.1115@4.16 | RBPIZRWOMRMEOB-ADDAZVEVSA-N | 0.124466377 | 0 | |
| 51 | 413.1115@4.16 | QEDMPKZKIAYWOT-UHFFFAOYSA-N | 0.136539354 | 0 | |
| 52 | 413.1115@4.16 | PWBXQAFXEBOSQR-UHFFFAOYSA-N | 0.120395741 | 0 | |
| 53 | 413.1115@4.16 | XSQXHRXJCIKADP-UHFFFAOYSA-N | 0.121674508 | 0 | |
| 54 | 413.1115@4.16 | XMAWYJWBFIGONN-UHFFFAOYSA-N | 0.121891621 | 0 | |
| 55 | 413.1115@4.16 | OQZAGOJJVQJMIE-ZTPQVCSDSA-N | 0.138834695 | 0 | |
| 56 | 413.1115@4.16 | RBPIZRWOMRMEOB-AGRNFKIVSA-N | 0.124466377 | 0 | |
| 57 | 413.1115@4.16 | VEDWXCWBMDQNCV-UHFFFAOYSA-N | 1.189274399 | 1 | JSTYUEOJPRFLHR-SCFUHWHPSA-N |
| 58 | 413.1115@4.16 | MWQHYFBKDKJTSZ-UHFFFAOYSA-N | 0.135087069 | 0 | |

| | compound_score | homology_score | reciprocal_score | query acc. | database_id_r2g | database_id_g2r |
|---|---|---|---|---|---|---|
| 1 | 0.648596239 | 400 | 2 | 637268597 | RXN-10622 | RXN-10622 |
| 2 | 0.188534242 | 1 | 0.1 | | | |
| 3 | 0.473961646 | 1 | 0.1 | | | |
| 4 | 0.473961735 | 1 | 0.1 | | | |
| 5 | 0.564805285 | 1 | 0.1 | | | |
| 6 | 0.649582665 | 1 | 0.1 | | | |
| 7 | 0.653333666 | 1 | 0.1 | | | |
| 8 | 0.653333666 | 1 | 0.1 | | | |
| 9 | 0.653333666 | 1 | 0.1 | | | |
| 10 | 0.832492644 | 1 | 0.1 | | | |
| 11 | 0.941043327 | 1 | 0.1 | | | |
| 12 | 1.030112081 | 1 | 0.1 | | | |
| 13 | 1.030240775 | 1 | 0.1 | | | |
| 14 | 0.373114888 | 120.1555874 | 2 | 637270405 | RHEA:12208 | RHEA:12208 |
| 15 | 0.648596239 | 42.32735177 | 2 | 637266239 | RHEA:26311 | RHEA:26311 |
| 16 | 0.941043327 | 1 | 0.1 | | | |
| 17 | 0.230117398 | 1 | 0.1 | | | |
| 18 | 0.18305083 | 1 | 0.1 | | | |
| 19 | 0.180715969 | 1 | 0.1 | | | |
| 20 | 0.170189484 | 1 | 0.1 | | | |
| 21 | 0.165005809 | 1 | 0.1 | | | |
| 22 | 0.149692331 | 1 | 0.1 | | | |
| 23 | 0.198447572 | 1 | 0.1 | | | |
| 24 | 0.137194586 | 1 | 0.1 | | | |
| 25 | 0.13194495 | 1 | 0.1 | | | |
| 26 | 0.292985333 | 400 | 2 | 637268765 | RHEA:33075 | RHEA:33075 |
| 27 | 0.395972143 | 1 | 0.1 | | | |
| 28 | 0.597785359 | 400 | 2 | 637268765 | RHEA:33075 | RHEA:33075 |
| 29 | 0.189090103 | 1 | 0.1 | | | |
| 30 | 0.222224088 | 1 | 0.1 | | | |
| 31 | 0.231920072 | 1 | 0.1 | | | |
| 32 | 0.260263169 | 1 | 0.1 | | | |
| 33 | 0.305326655 | 1 | 0.1 | | | |
| 34 | 0.286639518 | 1 | 0.1 | | | |
| 35 | 0.284255124 | 1 | 0.1 | | | |
| 36 | 0.353794564 | 1 | 0.1 | | | |
| 37 | 0.190671058 | 1 | 0.1 | | | |
| 38 | 0.28576021 | 1 | 0.1 | | | |
| 39 | 0.163959615 | 1 | 0.1 | | | |
| 40 | 0.169835458 | 1 | 0.1 | | | |
| 41 | 0.398100568 | 400 | 2 | 637268821 | RXN-10620 | RXN-10620 |
| 42 | 0.197319381 | 1 | 0.1 | | | |
| 43 | 0.196174645 | 1 | 0.1 | | | |
| 44 | 0.192491416 | 1 | 0.1 | | | |
| 45 | 0.190133981 | 1 | 0.1 | | | |
| 46 | 0.433526188 | 1 | 0.1 | | | |
| 47 | 0.636960054 | 400 | 2 | 637269940 | RHEA:40075 | RHEA:40075 |
| 48 | 0.330522777 | 1 | 0.1 | | | |
| 49 | 0.314263199 | 1 | 0.1 | | | |
| 50 | 0.239998315 | 1 | 0.1 | | | |
| 51 | 0.347561265 | 1 | 0.1 | | | |
| 52 | 0.210108922 | 1 | 0.1 | | | |
| 53 | 0.219178728 | 1 | 0.1 | | | |
| 54 | 0.220747302 | 1 | 0.1 | | | |
| 55 | 0.371528421 | 1 | 0.1 | | | |
| 56 | 0.239998315 | 1 | 0.1 | | | |
| 57 | 0.636960054 | 400 | 2 | 637269940 | RHEA:40075 | RHEA:40075 |
| 58 | 0.333008344 | 1 | 0.1 | | | |

TABLE 9A

Extended legend for FIG. 7A describing the reactions and compounds.

| Compound | Compound Name | inchikey |
|---|---|---|
| A | a 3,5,7,9,11,13,15-hepta-oxo-hexadecanoyl-[PKS-acp] | |
| B | 9-hydroxy-3,5,7,11,13,15-hexaoxohexadecanoyl-[PKS-acp] | |
| C | a (3'-hydroxy-2'-(3''-oxobutanoyl)phenyl)-3,5-dioxohexanethioate-[PKS-acp] | |
| D | 4-(3'-acetyl-5'-hydroxy-4'-oxo-1',4'-dihydronapthalen-2'-yl)-3-oxobutanoate-[PKS-acp] | |
| E | bicyclic intermediate E | PBONQNRANFYEQU-UHFFFAOYSA-N |
| F | bicyclic intermediate F | XORAIIJQEIRUFP-NSHDSACASA-N |
| G | S-hemiketal | YIEUIGLDTPWIHC-VQVVDHBBSA-N |
| H | S-DNPA | HHXSOTFPYPQSBU-LLVKDONJSA-N |
| I | 5-deoxy-dihydrokalafungin | BGCANOPAKSHGIV-KCJUWKMLSA-N |
| J | DHK-red | GBBQTBKHHWHZSJ-SFYZADRCSA-N |
| K | THN | YVNZMUZXESMJTM-RQJHMYQMSA-N |
| L | actinorhodin | VTIKDEXOEJDMJP-WYUUTHIRSA-N |
| M | dihydrokalafungin | ZCJHPTKRISJQTN-SFYZADRCSA-N |

TABLE 9B

Extended legend for FIG. 7B describing the reactions and compounds.

| Reaction | |
|---|---|
| 1 | RXN-12345 |
| 2 | RXN-15264 |
| 3 | RXN-14910 |
| 4 | RXN-9780 |
| 5 | RXN-10620 |
| 6 | RXN-10622 |
| 7 | RXN-12346 |

Correction of annotation errors. Gene annotation pipelines are notoriously error-prone and yield inconsistent results based on the bioinformatic analyses used: the database used for homology searches, and what kind of additional data (e.g. PFams, genetic neighborhoods, and literature mining) are incorporated into the annotation algorithm or not (see Table 3 for some examples). For example, the undecylprodigiosin synthase gene is known, yet was incorrectly annotated in the KEGG genome annotation for S. coelicolor. KEGG annotated this gene as "PEP utilizing enzyme" with an EC number of 2.7.9.2 (pyruvate, water phosphotransferase with paired electron acceptors). This is notable because the undecylprodigiosin synthase reaction has an EC number of 6.4.1.-: ligases that form carbon-carbon bonds. On the other hand, BioCyc correctly annotated SCO5896 as undecylprodigiosin synthase, presumably using manual curation or a thorough literature-searching algorithm.

Figure 8:
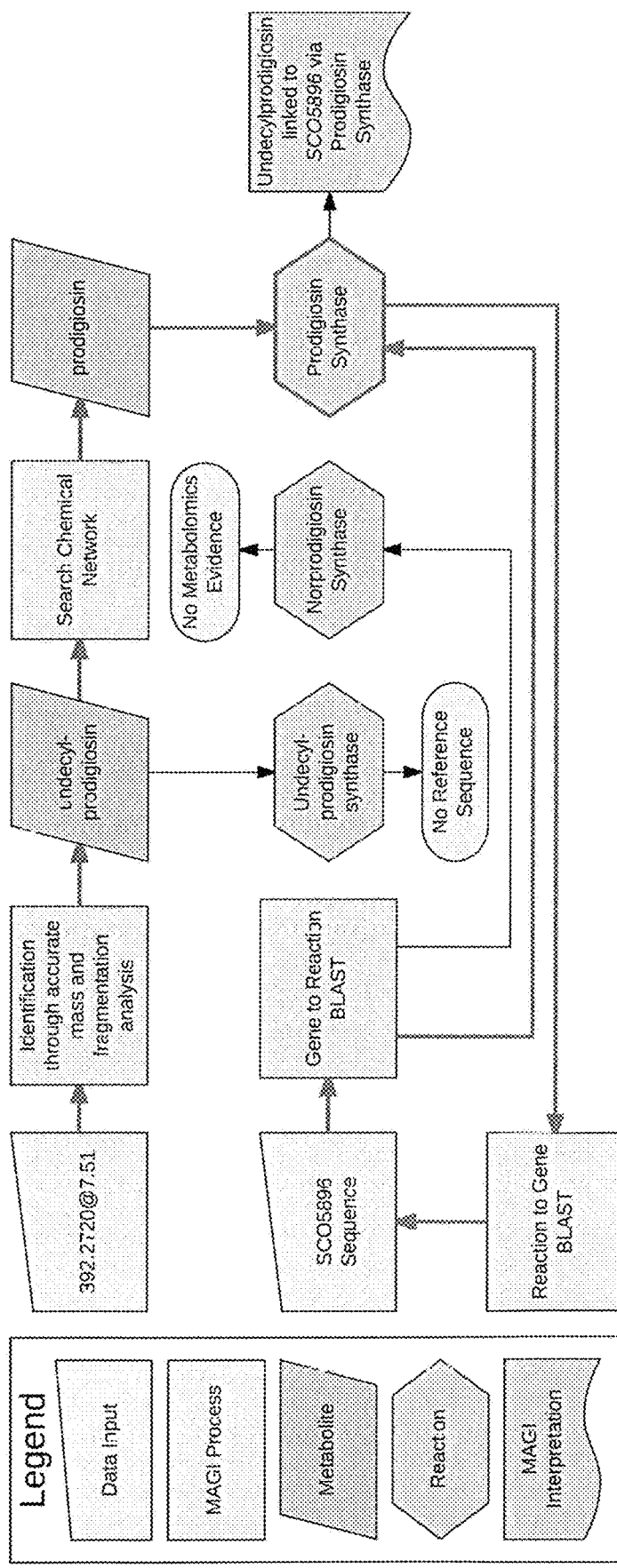
FIG. 8 is a flowchart illustrating the key components of the MAGI algorithm and process for associating undecylprodigiosin with SCO5896. In the upper half of the flowchart, the mass spectrometry feature with m/z 392.2720 at retention time 7.51 minutes was potentially identified to be undecylprodigiosin, which is in the undecylprodigiosin synthase reaction. This reaction has no reference sequence, so could not be directly connected to any *S. coelicolor* genes.

MAGI used metabolomics data to score the possible gene annotations for SCO5896 in addition to homology scoring (i.e. E-value). In the absence of metabolomics data, MAGI initially associated the SCO5896 gene sequence with the prodigiosin synthase and norprodigiosin synthase reactions via BLAST searches against the MAGI reaction reference sequence database (FIG. 8). Metabolomics analysis revealed that the feature with an m/z of 392.2720 could potentially be undecylprodigiosin, which MAGI associated with only the undecylprodigiosin synthase reaction (FIG. 8). Because this reaction does not have a reference sequence in our database, it could not be queried against the S. coelicolor genome. However, the chemical network revealed that prodigiosin is a similar metabolite that is in a reaction that does have a reference sequence (FIG. 8). When the prodigiosin synthase reaction's reference sequence was queried against the S. coelicolor genome, the top hit was SCO5896, thus making a reciprocal connection between the mass spectrometry feature and gene via the prodigiosin synthase reaction (FIG. 8).

Making nonexistent or vague annotations specific. The vast majority of sequenced genes have no discrete functional predictions, preventing the in-depth understanding of metabolic processes of most organisms. S. coelicolor is well known to produce several polyketides and is known to have the genetic potential to produce many more. The SCO5315 gene product is WhiE, a known polyketide aromatase involved in the biosynthesis of a white pigment characteristic of S. coelicolor. KEGG and BioCyC textually annotated the gene as "aromatase" or "polyketide aromatase," but neither link the gene to a discrete reaction. Although the text annotations are correct, the lack of a biochemical reaction prohibits the association of this gene with metabolites. On the other hand, MAGI was able to successfully associate SCO5315 with an observed metabolite (20-carbon polyketide intermediate with an m/z of 401.0887) via a polyketide cyclization reaction with a MAGI consensus score of 4.59 (Table 3). While the physiological function of WhiE is to cyclize a 24-carbon polyketide intermediate, the enzyme has been shown to also catalyze the cyclization of similar polyketides with varying chain length, including the 20-carbon species observed in the metabolomics data presented here.

In another example where other annotation services were unable to assign any reactions to a gene product, MAGI associated SCO7595 with the anhydro-NAM kinase reaction via the detected metabolite anhydro-N-acetylmuramic acid (anhydro-NAM) (m/z 274.0941) (Table 3). Anhydro-NAM is an intermediate in bacterial cell wall recycling, a critically important and significant metabolic process in actively growing bacterial cells; E. coli and other bacteria were observed to recycle roughly half of cell wall components per generation. MAGI also associated anhydro-NAM to SCO6300 via an acetylhexosaminidase reaction (Table3) that produces the metabolite. KEGG and RAST both annotated this gene to be acetylhexosaminidase with a total of 5 possible reactions, but none involved anhydro-NAM (Table 3). The detection of anhydro-NAM may be considered orthogonal experimental evidence to indicate that SCO6300 can act on N-acetyl-P-D-glucosamine-anhydro-NAM along with the other acetylhexosamines predicted by KEGG and RAST, forming an early stage in anhydromurpoeptide recycling. In the absence of MAGI, a researcher may have been able to manually curate a metabolic model by manually assessing the text annotations and adding reactions to the model, but the MAGI framework not only makes this process easier, it also connects an experimental observation that supports the predicted function of the gene.

Novel annotations. In addition to these few examples, there are hundreds more gene-reaction-metabolite associations that could be used to strengthen, validate, or correct existing annotations from KEGG or BioCyc, as well as discover new annotations through experimentation. These MAGI associations can be sorted by their MAGI score to generate a ranked list of candidate genes and gene functions, optionally hierarchically grouping and filtering the list by homology, metabolite, chemical network, and/or reciprocal score. For example, of the 1,883 S. coelicolor genes that were uniquely linked to a metabolite via a reaction by MAGI, roughly one-third were connected directly to a metabolite; that is, the chemical similarity network was not used to expand reaction space (FIG. 9A and FIG. 6C teal markers). Furthermore, one-third of these genes had perfect reciprocal agreement between the metabolite-to-gene and gene-to-metabolite search directions (FIG. 9B and FIG. 6C teal circles). These 190 genes can be further separated or binned based on their homology score or MAGI score (FIG. 5C), resulting in an actionable number of high-priority and high-strength novel gene function hypotheses to test in future studies.

Conclusion

Connecting metabolomics observations with genomic predictions helps overcome the limitations of each and strengthen the biological conclusions made by both. Metabolomics has the potential to aid gene annotations, and metabolic reconstructions of a genome can greatly simplify analyzing metabolomics data. The example introduced MAGI as a new tool for integrating these two types of measurements using Bayesian-like consensus scoring. Demonstrations here show that MAGI strengthens metabolite identifications, suggests specific biochemical predictions about genes that may otherwise be ambiguous, and suggests new biochemistry via the chemical network. Although nothing can replace traditional, small-scale directed biochemical and genetic studies, MAGI allows researchers to easily identify and direct those studies, resulting in stronger gene annotations and more complete and accurate metabolic reconstructions and models. In order to facilitate broad usage by the academic community, we provide MAGI through the National Energy Research Scientific Computing Center (NERSC) at magi.nersc.gov, where users can upload their own metabolite and FASTA files for analysis through MAGI.

REFERENCES

The content of each of the below references is incorporated herein by reference in its entirety.

1 Liu, X. J. & Locasale, J. W. Metabolomics: A Primer. Trends in Biochemical Sciences/12, 274-284, doi:10.1016/j.tibs.2017.01.004 (2017).

2 Zampieri, M., Sekar, K., Zamboni, N. & Sauer, U. Frontiers of high-throughput metabolomics. Current Opinion in Chemical Biology 36, 15-23, doi:10.1016/j.cbpa.2016.12.006 (2017).

3 Kell, D. B. & Oliver, S. G. The metabolome 18 years on: a concept comes of age. Metabolomics 12, doi:ARTN 148 10.1007/s11306-016-1108-4 (2016).

4 Saito, K. & Matsuda, F. Metabolomics for Functional Genomics, Systems Biology, and Biotechnology. Annu Rev Plant Biol 61, 463-489, doi:10.1146/annurev.arplant.043008.092035 (2010).

5 Creek, D. J. et al. Metabolite identification: are you sure? And how do your peers gauge your confidence? Metabolomics 10, 350-353, doi:10.1007/s11306-014-0656-8 (2014).

6 Wolfender, J. L., Marti, G., Thomas, A. & Bertrand, S. Current approaches and challenges for the metabolite profiling of complex natural extracts. J Chromatogr A 1382, 136-164, doi:10.1016/j.chroma.2014.10.091 (2015).

7 Vaniya, A. & Fiehn, O. Using fragmentation trees and mass spectral trees for identifying unknown compounds in metabolomics. Trac-Trend Anal Chem 69, 52-61, doi: 10.1016/j.trac.2015.04.002 (2015).

8 Smith, C. A. et al. METLIN: a metabolite mass spectral database. Ther Drug Monit 27, 747-751 (2005).

9 Horai, H. et al. MassBank: a public repository for sharing mass spectral data for life sciences. J Mass Spectrom 45, 703-714, doi:10.1002/jms.1777 (2010).

10 Wang, Y., Kora, G., Bowen, B. P. & Pan, C. MIDAS: a database-searching algorithm for metabolite identification in metabolomics. Anal Chem 86, 9496-9503, doi:10.1021/ac5014783 (2014).

11 Wolf, S., Schmidt, S., Muller-Hannemann, M. & Neumann, S. In silico fragmentation for computer assisted identification of metabolite mass spectra. BMC Bioinformatics 11, 148, doi:10.1186/1471-2105-11-148 (2010).

12 Allen, F., Greiner, R. & Wishart, D. Competitive fragmentation modeling of ESI-MS/MS spectra for putative metabolite identification. Metabolomics 11, 98-110, doi: 10.1007/s11306-014-0676-4 (2015).

13 Ridder, L. et al. Automatic Chemical Structure Annotation of an LC-MSn Based Metabolic Profile from Green Tea. Analytical Chemistry 85, 6033-6040, doi:10.1021/ac400861a (2013).

14 Duhrkop, K., Shen, H. B., Meusel, M., Rousu, J. & Bocker, S. Searching molecular structure databases with tandem mass spectra using CSI:FingerID. Proceedings of the National Academy of Sciences of the United States of America 112, 12580-12585, doi:10.1073/pnas.1509788112 (2015).

15 Dhanasekaran, A. R., Pearson, J. L., Ganesan, B. & Weimer, B. C. Metabolome searcher: a high throughput tool for metabolite identification and metabolic pathway mapping directly from mass spectrometry and using genome restriction. Bmc Bioinformatics 16, doi:ARTN 62 10.1186/s12859-015-0462-y (2015).

16 Li, S. Z. et al. Predicting Network Activity from High Throughput Metabolomics. Plos Computational Biology 9, doi:ARTN e1003123 10.1371/journal.pcbi.1003123 (2013).

17 Caspi, R. et al. The MetaCyc database of metabolic pathways and enzymes and the BioCyc collection of pathway/genome databases. Nucleic Acids Research 44, D471-D480, doi:10.1093/nar/gkv1164 (2016).

18 Morgat, A. et al. Updates in Rhea—an expert curated resource of biochemical reactions. Nucleic Acids Research 45, D415-D418, doi:10.1093/nar/gkw990 (2017).

19 Yang, J. Y. et al. Molecular Networking as a Dereplication Strategy. J Nat Prod 76, 1686-1699, doi:10.1021/np400413s (2013).

20 Hadadi, N., Hafner, J., Shajkofci, A., Zisaki, A. & Hatzimanikatis, V. ATLAS of Biochemistry: A Repository of All Possible Biochemical Reactions for Synthetic Biology and Metabolic Engineering Studies. Acs Synthetic Biology 5, 1155-1166, doi:10.1021/acssynbio.6b00054 (2016).

21 Hatzimanikatis, V. et al. Exploring the diversity of complex metabolic networks. Bioinformatics 21, 1603-1609, doi:10.1093/bioinformatics/bti213 (2005).

22 Li, C. H. et al. Computational discovery of biochemical routes to specialty chemicals. Chem Eng Sci 59, 5051-5060, doi:10.1016/j.ces.2004.09.021 (2004).

23 Hattori, M., Tanaka, N., Kanehisa, M. & Goto, S. SIMCOMP/SUBCOMP: chemical structure search servers for network analyses. Nucleic Acids Res 38, W652-656, doi:10.1093/nar/gkq367 (2010).

24 Temperton, B. & Giovannoni, S. J. Metagenomics: microbial diversity through a scratched lens. Curr Opin Microbiol 15, 605-612, doi:10.1016/j.mib.2012.07.001 (2012).

25 Aziz, R. K. et al. The RAST server: Rapid annotations using subsystems technology. Bmc Genomics 9, doi:Artn 75 10.1186/1471-2164-9-75 (2008).

26 Kanehisa, M., Sato, Y., Kawashima, M., Furumichi, M. & Tanabe, M. KEGG as a reference resource for gene and protein annotation. Nucleic Acids Research 44, D457-D462, doi:10.1093/nar/gkv1070 (2016).

27 Wu, C. H., Huang, H. Z., Yeh, L. S. L. & Barker, W. C. Protein family classification and functional annotation. Comput Biol Chem 27, 37-47, doi: 10.1016/S1476-9271(02)00098-1 (2003).

28 Craney, A., Ahmed, S. & Nodwell, J. Towards a new science of secondary metabolism. J Antibiot 66, 387-400, doi:10.1038/ja.2013.25 (2013).

29 Pluskal, T., Castillo, S., Villar-Briones, A. & Oresic, M. MZmine 2: modular framework for processing, visualizing, and analyzing mass spectrometry-based molecular profile data. BMC Bioinformatics 11, 395, doi:10.1186/1471-2105-11-395 (2010).

30 Bowen, B. P. & Northen, T. R. Dealing with the unknown: metabolomics and metabolite atlases. J Am Soc Mass Spectrom 21, 1471-1476, doi:10.1016/j.jasms.2010.04.003 (2010).

31 Hattori, M., Okuno, Y., Goto, S. & Kanehisa, M. Development of a chemical structure comparison method for integrated analysis of chemical and genomic information in the metabolic pathways. J Am Chem Soc 125, 11853-11865, doi:10.1021/ja036030u (2003).

32 Moriya, Y., Itoh, M., Okuda, S., Yoshizawa, A. C. & Kanehisa, M. KAAS: an automatic genome annotation and pathway reconstruction server. Nucleic Acids Res 35, W182-185, doi:10.1093/nar/gkm321 (2007).

33 Oellien, F., Cramer, J., Beyer, C., Ihlenteldt, W. D. & Selzer, P. M. The impact of tautomer forms on pharmacophore-based virtual screening. J Chem Inf Model 46, 2342-2354, doi:10.1021/ci060109b (2006).

34 Huan, T. et al. Systems biology guided by XCMS Online metabolomics. Nature Methods 14, 461-462 (2017).

35 Hiratsuka, T. et al. An alternative menaquinone biosynthetic pathway operating in microorganisms. Science 321, 1670-1673, doi:10.1126/science.1160446 (2008).

36 Mahanta, N., Fedoseyenko, D., Dairi, T. & Begley, T. P. Menaquinone Biosynthesis: Formation of Aminofutalosine Requires a Unique Radical SAM Enzyme. Journal of the American Chemical Society 135, 15318-15321, doi:10.1021/ja408594p (2013).

37 Nowicka, B. & Kruk, J. Occurrence, biosynthesis and function of isoprenoid quinones. Bba-Bio energetics 1797, 1587-1605, doi:10.1016/j.bbabio.2010.06.007 (2010).

38 Schnoes, A. M., Brown, S. D., Dodevski, I. & Babbitt, P. C. Annotation Error in Public Databases: Misannotation of Molecular Function in Enzyme Superfamilies. Plos Computational Biology 5, doi:ARTN e1000605 10.1371/journal.pcbi.1000605 (2009).

39 Haynes, S. W., Sydor, P. K., Stanley, A. E., Song, L. J. & Challis, G. L. Role and substrate specificity of the *Streptomyces coelicolor*, RedH enzyme in undecylprodiginine biosynthesis. Chem Commun, 1865-1867, doi:10.1039/b801677a (2008).

40 Shen, Y. M. et al. Ectopic expression of the minimal whiE polyketide synthase generates a library of aromatic polyketides of diverse sizes and shapes. Proceedings of the National Academy of Sciences of the United States of America 96, 3622-3627, doi:DOI 10.1073/pnas.96.7.3622 (1999).

41 Yu, T. W. et al. Engineered biosynthesis of novel polyketides from *Streptomyces* spore pigment polyketide synthases. Journal of the American Chemical Society 120, 7749-7759, doi:DOI 10.1021/ja9803658 (1998).

42 Alvarez, M. A., Fu; H., Khosla, C., Hopwood, D. A. & Bailey, J. E. Engineered biosynthesis of novel polyketides: Properties of the whiE aromatase/cyclase. Nature Biotechnology 14, 335-338, doi:DOI 10.1038/nbt0396-335 (1996).

43 Mcdaniel, R., Hutchinson, C. R. & Khosla, C. Engineered Biosynthesis of Novel Polyketides—Analysis of Tcmn Function in Tetracenomycin Biosynthesis. Journal of the American Chemical Society 117, 6805-6810, doi:DOI 10.1021/ja00131a001 (1995).

44 Ames, B. D. et al. Crystal structure and functional analysis of tetracenomycin ARO/CYC: Implications for cyclization specificity of aromatic polyketides. Proceedings of the National Academy of Sciences of the United States of America 105, 5349-5354, doi:10.1073/pnas.0709223105 (2008).

45 Park, J. T. & Uehara, T. How bacteria consume their own exoskeletons (Turnover and recycling of cell wall peptidoglycan). Microbiology and Molecular Biology Reviews 72, 211-227, doi:10.1128/Mmbr.00027-07 (2008).

46 Johnson, J. W., Fisher, J. F. & Mobashery, S. Bacterial cell-wall recycling. Ann Ny Acad Sci 1277, 54-75, doi: 10.1111/j.1749-6632.2012.06813.x (2013).

47 Cooper, L. E. et al. In Vitro Reconstitution of the Radical S-Adenosylmethionine Enzyme MqnC Involved in the Biosynthesis of Futalosine-Derived Menaquinone. Biochemistry 52, 4592-4594, doi:10.1021/bi400498d (2013).

48 Ichinose, K. et al. Proof that the actVI genetic region of *Streptomyces coelicolor* A3(2) is involved in stereospecific pyran ring formation in the biosynthesis of actinorhodin. Bioorganic & Medicinal Chemistry Letters 9, 395-400, doi:Doi 10.1016/S0960-894x(99)00011-6 (1999).

49 Taguchi, T. et al. Chemical characterisation of disruptants of the *Streptomyces coelicolor* A3(2) actVl genes involved in actinorhodin biosynthesis. J Antibiot 53, 144-152 (2000).

50 Valton, J., Filisetti, L., Fontecave, M. & Niviere, V. A two-component flavin-dependent monooxygenase involved in actinorhodin biosynthesis in *Streptomyces coelicolor*. Journal of Biological Chemistry 279, 44362-44369, doi: 10.1074/jbc.M407722200 (2004).

51 Kendrew, S. G., Hopwood, D. A. & Marsh, E. N. G. Identification of a monooxygenase from *Streptomyces coelicolor* A3(2) involved in biosynthesis of actinorhodin: Purification and characterization of the recombinant enzyme. Journal of Bacteriology 179, 4305-4310 (1997).

52 Mcdaniel, R., Ebertkhosla, S., Fu, H., Hopwood, D. A. & Khosla, C. Engineered Biosynthesis of Novel Polyketides—Influence of a Downstream Enzyme on the Catalytic Specificity of a Minimal Aromatic Polyketide Synthase. Proceedings of the National Academy of Sciences of the United States of America 91, 11542-11546, doi:DOI 10.1073/pnas.91.24.11542 (1994).

53 Onur Erbilgin, Oliver Ruebel, Katherine B Louie, Matthew Trinh, Markus de Raad, Tony Wildish, Daniel W Udwary, Cindi A Hoover, Samuel Deutsch, Trent R Northen, Benjamin P Bowen. MAGI: A Bayesian-like method for metabolite, annotation, and gene integration. bioRxiv 20/1362; doi: https://doi.org/10.1101/204362

Terminology

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for associating metabolites with genes comprising:
    a non-transitory memory configured to store executable instructions; and
    a hardware processor in communication with the non-transitory memory, the hardware processor programmed by executable instructions to perform:
        receiving and storing metabolite spectroscopy data, obtained from a content of an organism, and a genome sequence of the organism, in a database;
        identifying a plurality of potential metabolites from the content of the organism in the metabolite spectroscopy data;
        determining, for each of the plurality of potential metabolites, one or more first possible reactions related to the potential metabolite;
        determining, for each of the first possible reactions, one or more first genes with corresponding gene products involved in the first possible reaction from the genome sequence;
        determining, for each of the plurality of potential metabolites, an association score indicating a likelihood that a first gene of the first genes is associated with the potential metabolite;
        generating at least one experiment design of a biochemical experiment based on the association score of at least one of the plurality of potential metabolites;
        providing the at least one experiment design of the biochemical experiment to one or more laboratory instruments which perform the biochemical experiment to validate the first gene of the first genes is associated with the potential metabolite; and updating the database with results from the biochemical experiment, the updating comprising supplementing or replacing existing annotations in the database with new reactions and reference sequences to reactions, wherein determining, for each of the plurality of potential metabolites, one or more first possible reactions related to the potential metabolite comprises:

determining a related metabolite of a potential metabolite of the plurality of potential metabolites; and determining one or more first possible reactions related to the related metabolite, wherein the one or more first possible reactions related to the related metabolite are one or more first possible reactions related to the potential metabolite.

2. The system of claim 1, wherein the metabolite spectroscopy data comprises liquid chromatography mass spectrometry (LCMS) data obtained from the content of the organism.

3. The system of claim 2, wherein the LCMS data comprises a plurality of MS/MS spectra.

4. The system of claim 1, wherein identifying the plurality potential metabolites in the content of the organism in the metabolite spectroscopy data comprises identifying the plurality of potential metabolites based on metabolite features in the metabolite spectroscopy data.

5. The system of claim 4, wherein each metabolite feature comprises a retention time, a m/z value, a mass spectrometry (MS) adduct value, a fragmentation pattern, or any combination thereof.

6. The system of claim 4, wherein identifying the plurality of potential metabolites in the content of the organism comprises determining a metabolite score indicating a correspondence between the structure of each potential metabolite and one or more of the metabolite features.

7. The system of claim 1, wherein determining the one or more first genes with corresponding gene products involved in the first possible reactions comprises:

determining one or more second genes of the organism associated with one or more of the first possible reactions based on sequences of the first genes, sequences of the second genes, sequences of gene products of the first genes, and/or sequences of gene products of the second genes; and determining one or more second possible reactions associated the first genes.

8. The system of claim 7, wherein the hardware processor is further programmed by the executable instructions to perform:

determining a homology score indicating the first gene and each second gene being homologs;

determining a reciprocal agreement score indicating agreement between the first possible reaction and each second possible reaction; and performing metabolite identification and/or gene annotation based on the metabolite score, the homology score, the reciprocal agreement score, and/or an aggregate score of the metabolite score, the homology score, and the reciprocal score.

9. The system of claim 8, wherein the homology score is determined based on a reaction-to-gene score associated with determining the one or more second genes and a gene-to-reaction score associated with determining the one or more second possible reactions.

10. The system of claim 8, wherein the aggregate score is determined based on a geometric mean of the metabolite score, the homology score, and the reciprocal agreement score.

11. The system of claim 10, wherein the aggregate score is determined based on a network level connecting the potential metabolite to the first possible reaction and a penalty factor for the network level.

12. The system of claim 8, wherein determining the one or more first possible reactions related to the potential metabolite comprises determining a metabolite score of each related metabolite based on the metabolite score of the potential metabolite.

13. The system of claim 1, wherein the related metabolites comprise tautomers of the potential metabolite.

14. The system of claim 1, wherein determining the one or more related metabolites comprises determining the one or more related metabolites from the potential metabolite using a chemical network.

15. The system of claim 14, wherein the chemical network relates the potential metabolite to the one or more related metabolites by biochemical similarity.

16. The system of claim 15, wherein the biochemical similarity is determined based on chemical features of the potential metabolite and each related metabolite of the potential metabolite.

17. A method for determining metabolite-gene associations, comprising:

receiving and storing liquid chromatography mass spectrometry (LCMS) data obtained from a sample comprising a plurality of metabolites of an organism in a database;

determining one or more of a metabolite score, a homology score, a reciprocal agreement score, and an aggregate score for each of a plurality of metabolite-reaction-gene associations based on the LCMS data;

performing an analysis of one or more of the metabolite score, the homology score, the reciprocal agreement score, and the aggregate score to determine an association between at least one metabolite of the plurality of metabolites of the organism and a gene of a plurality of genes of the organism;

generating at least one experiment design of a high-throughput biochemical experiment based on the at least one metabolite of the plurality of metabolites of the organism and the gene of the plurality of genes of the organism;

performing the high-throughput biochemical experiment using one or more laboratory instruments comprising a microfluidics device and a mass spectrometer to validate the association between the at least one metabolite of the plurality of metabolites of the organism and the gene of the plurality of genes of the organism; and updating the database with results from the high-throughput biochemical experiment, the updating comprising supplementing or replacing existing annotations in the database with new reactions and reference sequences to reactions.

18. The method of claim 17, wherein performing the analysis comprising performing metabolite identification.

19. The method of claim 18, wherein performing metabolite identification comprises selecting a top scoring metabolite-reaction-gene association for each metabolite.

20. The method of claim 17, wherein performing the analysis comprises performing gene annotation.

21. The method of claim 20, wherein performing gene annotation comprises selecting a top scoring metabolite-reaction-gene association for each gene-reaction pair.

22. The method of claim 17, wherein determining the metabolite score comprises: determining a metabolite score based on one or more metabolite features corresponding to the metabolite in the LCMS data.

23. The method of claim 22, wherein determining the homology score and the reciprocal agreement score comprises:
    determining one or more first reactions involving each metabolite, wherein each first reaction is associated with a first gene sequence with a corresponding gene product involved in the first reaction;
    determining one or more second gene sequences of the organism related to each first reaction based on the associated first gene sequence;
    determining one or more second reactions related to the first gene sequence based on the one or more second gene sequences;
    determining the homology score indicating the first gene sequence and each second gene sequence being homologs; and
    determining the reciprocal agreement score indicating agreement between the first reaction and each second reaction.

24. The system of claim 1, wherein the first possible reactions related to the potential metabolite comprises a first possible reaction capable of producing the potential metabolite and a second possible reaction incapable of producing the potential metabolite.

25. The system of claim 12, wherein at least one first possible reactions of the first possible reactions is capable of producing at least one of the one or more related metabolites of the potential metabolite, and wherein at least another first possible reactions of the first possible reactions is incapable of producing any of the one or more related metabolites of the potential metabolite.

26. A system for associating metabolites with genes comprising:
    a biochemical assertion manager for organizing and storing experimental data inputs, a plurality of genes, a plurality of chemical compounds, and a plurality of reactions each associated with one or more genes of the plurality of genes and one or more chemical compounds of the plurality of chemical compounds;
    a hypothesis generation module for generating one or both of compound-centric hypothesis based on chemicals compounds of the plurality of chemical compounds present in the experimental data inputs and the plurality of reactions and gene-centric hypothesis based on the plurality of genes;
    a biochemical experiment design module for designing biochemical experiments for testing one or both of compound-centric hypothesis and gene-centric hypothesis generated;
    a controller for instructing one or more laboratory instruments, the one or more laboratory instruments comprising a reagent handling equipment, mass spectrometer, a nuclear magnetic resonance (NMR) spectrometer, and/or a sequencer, to perform the designed biochemical experiments;
    a data store for storing the experimental data inputs, the plurality of genes, the plurality of chemical compounds, the plurality of reactions, the compound-centric hypothesis and drug-centric hypothesis generated, and results of the biochemical experiments designed.

* * * * *